(12) United States Patent
Tehrani et al.

(10) Patent No.: US 8,200,336 B2
(45) Date of Patent: Jun. 12, 2012

(54) SYSTEM AND METHOD FOR DIAPHRAGM STIMULATION

(75) Inventors: Amir J. Tehrani, Redwood City, CA (US); David Ligon, Redwood City, CA (US)

(73) Assignee: RMX, LLC, San Francisco, CA (US)

( * ) Notice: Subject to any disclaimer, the term of this patent is extended or adjusted under 35 U.S.C. 154(b) by 1149 days.

(21) Appl. No.: 10/966,472

(22) Filed: Oct. 15, 2004

(65) Prior Publication Data

US 2005/0085867 A1 Apr. 21, 2005

Related U.S. Application Data

(63) Continuation-in-part of application No. 10/686,891, filed on Oct. 15, 2003.

(51) Int. Cl.
*A61N 1/08* (2006.01)
(52) U.S. Cl. ......................................................... 607/42
(58) Field of Classification Search ...................... 607/42
See application file for complete search history.

(56) References Cited

U.S. PATENT DOCUMENTS

| | | | |
|---|---|---|---|
| 3,773,051 A | 11/1973 | Holcomb et al. | |
| 4,827,935 A | 5/1989 | Geddes et al. | |
| 4,830,008 A | 5/1989 | Meer | 128/421 |
| 5,056,519 A | 10/1991 | Vince | 128/419 |
| 5,146,918 A | 9/1992 | Kallok et al. | 128/419 |
| 5,174,287 A | 12/1992 | Kallok et al. | 128/419 |
| 5,190,036 A * | 3/1993 | Linder | 607/42 |
| 5,211,173 A | 5/1993 | Kallok et al. | 128/419 |
| 5,215,082 A | 6/1993 | Kallok et al. | 128/419 |
| 5,233,983 A | 8/1993 | Markowitz | 607/42 |
| 5,265,604 A | 11/1993 | Vince | 607/42 |
| 5,281,219 A | 1/1994 | Kallok | 607/42 |
| 5,300,094 A | 4/1994 | Kallok et al. | 607/42 |
| 5,423,327 A | 6/1995 | Clauson et al. | 128/716 |
| 5,483,969 A | 1/1996 | Testerman et al. | |
| 5,485,851 A | 1/1996 | Erickson | 128/716 |
| 5,522,862 A | 6/1996 | Testerman et al. | 607/42 |
| 5,524,632 A | 6/1996 | Stein et al. | 128/733 |
| 5,540,731 A | 7/1996 | Testerman | 607/42 |

(Continued)

FOREIGN PATENT DOCUMENTS

DE 112004001957 T5 8/2006

(Continued)

OTHER PUBLICATIONS

Vander et al., Human Physiology: The Mechanisms of Body Function, 2001, McGraw-Hill, 8th edition, pp. 470-471.*

(Continued)

*Primary Examiner* — Niketa Patel
*Assistant Examiner* — Alyssa M Alter
(74) *Attorney, Agent, or Firm* — Levine Bagade Han LLP

(57) ABSTRACT

A stimulation device is provided that stimulates breathing to manipulate blood gas concentrations such as $SaO_2$ or $PCO_2$ and thereby treat underlying causes of breathing disorders and heart failure progression. A programmable device is provided for setting diaphragm stimulation waveforms that adjust minute ventilation about a predetermined baseline value. Normal breathing of the subject is observed to establish a baseline reference minute ventilation, and the device is programmed to produce stimulation waveforms that may provide either a decrease or an increase in the patients minute ventilation. The minute ventilation of the subject may be decreased or increased from the baseline level by decreasing or increasing a parameter that changes minute ventilators.

33 Claims, 26 Drawing Sheets

U.S. PATENT DOCUMENTS

| | | | |
|---|---|---|---|
| 5,540,732 A | 7/1996 | Testerman et al. | 607/42 |
| 5,540,733 A | 7/1996 | Testerman et al. | 607/42 |
| 5,546,952 A | 8/1996 | Erickson | |
| 5,549,655 A | 8/1996 | Erickson | |
| 5,572,543 A | 11/1996 | Heinemann et al. | |
| 5,678,535 A | 10/1997 | DiMarco | 128/200.24 |
| 5,766,228 A | 6/1998 | Bonnet et al. | 607/16 |
| 5,797,923 A | 8/1998 | Aiyar et al. | 606/129 |
| 5,800,470 A | 9/1998 | Stein et al. | 607/20 |
| 5,814,086 A | 9/1998 | Hirschberg et al. | |
| 5,830,008 A | 11/1998 | Broschard, III | |
| 5,876,353 A | 3/1999 | Riff | 600/547 |
| 5,895,360 A | 4/1999 | Christopherson et al. | 600/529 |
| 5,911,218 A | 6/1999 | DiMarco | 128/200.24 |
| 5,944,680 A | 8/1999 | Christopherson et al. | |
| 6,021,352 A | 2/2000 | Christopherson et al. | 607/42 |
| 6,099,479 A | 8/2000 | Christopherson et al. | 600/529 |
| 6,212,435 B1 | 4/2001 | Lattner et al. | 607/134 |
| 6,224,562 B1 | 5/2001 | Lurie et al. | 601/41 |
| 6,251,126 B1 | 6/2001 | Ottenhoff et al. | 607/42 |
| 6,269,269 B1 | 7/2001 | Ottenhoff et al. | 607/42 |
| 6,312,399 B1 * | 11/2001 | Lurie et al. | 601/41 |
| 6,314,324 B1 | 11/2001 | Lattner et al. | |
| 6,345,202 B2 | 2/2002 | Richmond et al. | 607/42 |
| 6,415,183 B1 | 7/2002 | Scheiner et al. | 607/42 |
| 6,463,327 B1 | 10/2002 | Lurie et al. | |
| 6,480,733 B1 | 11/2002 | Turcott | 600/516 |
| 6,489,447 B1 | 12/2002 | Basey et al. | |
| 6,512,949 B1 | 1/2003 | Combs et al. | |
| 6,527,729 B1 | 3/2003 | Turcott | 600/528 |
| 6,542,774 B2 | 4/2003 | Hill et al. | |
| 6,572,543 B1 | 6/2003 | Christopherson et al. | 600/300 |
| 6,574,507 B1 | 6/2003 | Bonnet | 607/20 |
| 6,587,725 B1 | 7/2003 | Durand et al. | |
| 6,587,726 B2 | 7/2003 | Lurie et al. | |
| 6,589,188 B1 | 7/2003 | Street et al. | 600/538 |
| 6,600,949 B1 | 7/2003 | Turcott | 600/518 |
| 6,633,779 B1 | 10/2003 | Schuler et al. | |
| 6,651,652 B1 | 11/2003 | Ward | 128/200.24 |
| 6,731,984 B2 | 5/2004 | Cho et al. | 607/17 |
| 6,735,479 B2 | 5/2004 | Fabian et al. | |
| 6,752,765 B1 | 6/2004 | Jensen et al. | 600/536 |
| 6,770,022 B2 | 8/2004 | Mechlenburg et al. | |
| 6,811,537 B2 | 11/2004 | Bardy | |
| 6,830,548 B2 | 12/2004 | Bonnet et al. | 600/529 |
| 6,881,192 B1 | 4/2005 | Park | |
| 6,908,437 B2 | 6/2005 | Bardy | |
| 7,058,453 B2 | 6/2006 | Nelson et al. | |
| 7,070,568 B1 | 7/2006 | Koh et al. | |
| 7,082,331 B1 | 7/2006 | Park et al. | |
| 7,117,032 B2 | 10/2006 | Childre et al. | |
| 7,277,757 B2 | 10/2007 | Casavant et al. | |
| 7,532,934 B2 | 5/2009 | Lee et al. | |
| 7,610,094 B2 | 10/2009 | Stahmann et al. | |
| 7,840,270 B2 | 11/2010 | Ignagni et al. | |
| 7,970,475 B2 | 6/2011 | Tehrani et al. | |
| 7,979,128 B2 | 7/2011 | Tehrani et al. | |
| 8,116,872 B2 | 2/2012 | Tehrani et al. | |
| 2002/0049482 A1 | 4/2002 | Fabian et al. | |
| 2002/0193697 A1 | 12/2002 | Cho et al. | |
| 2002/0193839 A1 | 12/2002 | Cho et al. | 607/17 |
| 2003/0127091 A1 | 7/2003 | Chang | |
| 2003/0153953 A1 | 8/2003 | Park et al. | 607/17 |
| 2003/0153954 A1 | 8/2003 | Park et al. | 607/17 |
| 2003/0153955 A1 | 8/2003 | Park et al. | 607/17 |
| 2003/0153956 A1 | 8/2003 | Park et al. | 607/17 |
| 2003/0195571 A1 | 10/2003 | Burnes et al. | 607/9 |
| 2003/0204213 A1 | 10/2003 | Jensen et al. | |
| 2003/0225339 A1 | 12/2003 | Orr et al. | |
| 2004/0044377 A1 | 3/2004 | Larsson | |
| 2004/0059240 A1 | 3/2004 | Cho et al. | |
| 2004/0077953 A1 | 4/2004 | Turcott | |
| 2004/0088015 A1 | 5/2004 | Casavant et al. | 607/14 |
| 2004/0111040 A1 | 6/2004 | Ni et al. | 600/534 |
| 2004/0116784 A1 | 6/2004 | Gavish | |
| 2004/0122484 A1 | 6/2004 | Hatlestad et al. | |
| 2004/0134496 A1 | 7/2004 | Cho et al. | 128/204.23 |
| 2004/0138719 A1 | 7/2004 | Cho et al. | 607/42 |
| 2004/0176809 A1 | 9/2004 | Cho et al. | 607/14 |
| 2004/0199221 A1 | 10/2004 | Fabian et al. | |
| 2004/0225226 A1 | 11/2004 | Lehrman et al. | 600/529 |
| 2004/0237963 A1 | 12/2004 | Berthon-Jones | 128/204.26 |
| 2005/0021102 A1 * | 1/2005 | Ignagni et al. | 607/42 |
| 2005/0039745 A1 | 2/2005 | Stahmann et al. | |
| 2005/0043644 A1 | 2/2005 | Stahmann et al. | 600/529 |
| 2005/0043772 A1 | 2/2005 | Stahmann et al. | |
| 2005/0055060 A1 | 3/2005 | Koh et al. | 607/17 |
| 2005/0061315 A1 | 3/2005 | Lee et al. | 128/204.21 |
| 2005/0061319 A1 | 3/2005 | Hartley et al. | 128/204.18 |
| 2005/0061320 A1 | 3/2005 | Lee et al. | 128/204.18 |
| 2005/0065563 A1 | 3/2005 | Scheiner | 607/9 |
| 2005/0065567 A1 | 3/2005 | Lee et al. | 607/17 |
| 2005/0074741 A1 | 4/2005 | Lee et al. | 434/433 |
| 2005/0076909 A1 | 4/2005 | Stahmann et al. | |
| 2005/0080461 A1 | 4/2005 | Stahmann et al. | 607/17 |
| 2005/0085734 A1 | 4/2005 | Tehrani | |
| 2005/0085865 A1 | 4/2005 | Tehrani | |
| 2005/0085866 A1 | 4/2005 | Tehrani | |
| 2005/0085868 A1 | 4/2005 | Tehrani et al. | |
| 2005/0085869 A1 | 4/2005 | Tehrani et al. | |
| 2005/0101833 A1 | 5/2005 | Hsu et al. | 600/26 |
| 2005/0107860 A1 | 5/2005 | Ignagni et al. | 607/116 |
| 2005/0115561 A1 | 6/2005 | Stahmann et al. | 128/200.24 |
| 2005/0119711 A1 | 6/2005 | Cho et al. | |
| 2005/0145246 A1 | 7/2005 | Hartley et al. | 128/203.14 |
| 2005/0148897 A1 | 7/2005 | Cho et al. | 600/533 |
| 2005/0165457 A1 | 7/2005 | Benser et al. | |
| 2005/0224076 A1 | 10/2005 | Pfichner et al. | |
| 2005/0240240 A1 | 10/2005 | Park et al. | 607/42 |
| 2005/0261600 A1 | 11/2005 | Aylsworth | |
| 2005/0261747 A1 | 11/2005 | Schuler et al. | |
| 2006/0030894 A1 | 2/2006 | Tehrani | |
| 2006/0036294 A1 | 2/2006 | Tehrani | |
| 2006/0058852 A1 | 3/2006 | Koh et al. | |
| 2006/0064030 A1 | 3/2006 | Cosentino et al. | |
| 2006/0064325 A1 | 3/2006 | Matsumoto et al. | |
| 2006/0122661 A1 | 6/2006 | Mandell | |
| 2006/0122662 A1 | 6/2006 | Tehrani | |
| 2006/0142815 A1 | 6/2006 | Tehrani et al. | |
| 2006/0149334 A1 | 7/2006 | Tehrani et al. | |
| 2006/0155341 A1 | 7/2006 | Tehrani et al. | |
| 2006/0167523 A1 | 7/2006 | Tehrani et al. | |
| 2006/0224211 A1 | 10/2006 | Durand et al. | |
| 2006/0247729 A1 | 11/2006 | Tehrani et al. | |
| 2006/0282131 A1 | 12/2006 | Caparso et al. | |
| 2007/0021795 A1 | 1/2007 | Tehrani | |
| 2007/0156199 A1 | 7/2007 | Koh et al. | |
| 2008/0021506 A1 | 1/2008 | Grocela | |
| 2008/0167695 A1 | 7/2008 | Tehrani et al. | |
| 2008/0177347 A1 | 7/2008 | Tehrani et al. | |
| 2008/0183239 A1 | 7/2008 | Tehrani et al. | |
| 2008/0183240 A1 | 7/2008 | Tehrani et al. | |
| 2008/0188903 A1 | 8/2008 | Tehrani et al. | |
| 2008/0188904 A1 | 8/2008 | Tehrani et al. | |
| 2008/0208281 A1 | 8/2008 | Tehrani et al. | |
| 2011/0230932 A1 | 9/2011 | Tehrani et al. | |

FOREIGN PATENT DOCUMENTS

| | | |
|---|---|---|
| DE | 112004001953 T5 | 10/2006 |
| DE | 112004001954 T5 | 10/2006 |
| WO | WO/8600234 | 1/1986 |
| WO | WO 2005/037077 | 4/2005 |
| WO | WO 2005/037172 | 4/2005 |
| WO | WO 2005/037173 | 4/2005 |
| WO | WO 2005/037174 | 4/2005 |
| WO | WO 2005/037220 | 4/2005 |
| WO | WO 2005/037366 | 4/2005 |
| WO | WO 2007/058938 | 5/2007 |

OTHER PUBLICATIONS

Don D. Sin, Effects of Continuous Positive Airway Pressure on Cardiovascular Outcomes in Heart Failure Patients With and Without Cheyne-Stokes Respiration, *Circulation*, 102:61-66 (Jul. 4, 2000).

Takaomi Taira, M.D., Ph.D., et. al, Phrenic Nerve Stimulation for Diaphragm Pacing With a Spinal Cord Stimulator *Surg Neurol*, 59:128-132 (2003).

Donald B. Shaul, et. al, Thoracoscopic Placement of Phrenic Nerve Electrodes for Diaphragmatic Pacing in Children *Journal of Pediatric Surgery*, 37:974-978 (Jul. 2002).
Christopher Reeve, New Implantable Breathing Device, *University Hospitals of Cleveland*, pp. 1-4. (2003).
Christopher Reeve, Christopher Reeve Paralysis Foundation Questions & Answers, pp. 1-3 (Mar. 13, 2003).
T. Mitsuyana, et. al, Diaphragm Pacing With the Spinal Cord Stimulator, *Aeta Neurochir*, 87:89-92 (2003).
Harish Aiyar, et. al, Laparoscopic Implant Device for Intermuscular Electrodes, IEEE-EMBC and CMBCC, pp. 1167-1168, ((1995).
Harish Aiyar,et.al, Laparoscopic Implant Instrument for the Placement of Intramuscular Electrodes in the Diaphragm, *Transactions on Rehabilitation Engineering*, pp. 360-371 (Sep. 1999).
Anthony F. DiMarco, et. al, Phrenic Nerve Pacing in a Tetraplegic Patient via Intramuscula Diaphragm Electrodes*American Journal of Respiratory and Critical Care Medicine*, 144:1604-1606 (2002).
S.Sauermann, et. al, Computer Aided Adjustment of the Phrenic Pacemaker: Automatic Functions, Documentation, and Quality Control, *Artificial Organs*, 21(3):216-218 (1997).
B.D. Schmit, et. al, An Implantable Impedance Pneumograph Monitor for Detection of Diaphragm Contraction and Airway Obstruction During Diaphragm Pacing, *Medical & Biological Engineering & Computing*,37:162-168 (1999).
Brian D. Schmit, et. al, Laparoscopic Placement of Electrodes for Diaphragm Pacing Using Stimulation to Locate the Phrenic Nerve Motor Points, *Transactions on Rehabilitation Engineering*, 6(4):382-390 (Dec. 1998).
W. Glenn "Diaphragm Pacing: Present Status" PACE vol. 1 p. 357-370 (1978).
L Bernardi et al "Effect of Rosary Prayer and Yoga Mantras on Autonomic Cardiovascular Rhythms: Comparative Study" BMJ vol. 323 (Dec. 22-29, 2001).
L Bernardi et al "Slow Breathing Increases Arterial Baroreflex sensitivity in Patients with Chronic Heart Failure" Circulation (2002).
A Jensen et al. Signal Transduction in Smooth Muscle: Airway caliber in healthy and asthmatic subjects effects of bronchial challenge and deep inspirations. J. Appl Physiol 91: 506-515 (2001).
W. Glenn et al: "Diaphragm Pacing" Journal of Thoracic and Cardiovascular Surgery vol. 75 No. 2, 273-281 (1978).
Patroniti M.D., et al "Sigh Improves Gas Exchange and Lung Volume in Patients with Acute Respiratory Distress Syndrome Undergoing Pressure Support Ventilation" Anesthesiology 96: 788-94 (2002).
R. Gosselink Controlled Breathing and Dyspnea in Patients With Chronic Obstructive Pulmonary Disease. Journal of Rehabilitaiton Research and Development vol. 40, No. 5 , Supplement 2 p. 20-34 (Sep./Oct. 2003).
Harish, A. et al, "Laparoscopic Implant Device for Intermuscular Electrodes," *IEEE-EMBC and CMBCC*, pp. 1167-1168, 1995.
Shier, D. et al, *Hole's Human Anatomy & Physiology*,pp. 798 (2 pages total).
U.S. Appl. No. 11/271,726, filed Nov. 10, 2005 in the name of Tehrani et al., Notice of Allowance mailed May 18, 2011.
U.S. Appl. No. 11/271,264, filed Nov. 10, 2005 in the name of Tehrani et al., Notice of Allowance mailed May 20, 2011.
Iazzo, P. ed., "Handbook of Cardiac Anatomy, Physiology, and Devices", p. 398, 2009.
Liem, L.B., "EP 101: Ventricular Tachycardia", EP Lab Digest, v.7, No. 8, Aug. 2007.
Malkin R. et al., "The Effect of Inducing Ventricular Fibrillation with 50-Hz Pacing Versus T are Stimulation on the Ability to Defibrillate", Pacing And Clinical Electrophysiology, vol. 21, issue 5, May 1998.
U.S. Appl. No. 11/249,718, filed Oct. 13, 2005 in the name of Tehrani, final Office Action mailed Sep. 14, 2010.
U.S. Appl. No. 10/686,891, filed Oct. 15, 2003 in the name of Tehrani, final Office Action mailed Sep. 15, 2010.
U.S. Appl. No. 11/526,949, filed Sep. 25, 2006 in the name of Tehrani, non-final Office Action mailed Oct. 5, 2010.
U.S. Appl. No. 11/981,342, filed Oct. 31, 2007 in the name of Tehrani et al., final Office Action mailed Oct. 7, 2010.
U.S. Appl. No. 11/271,554, filed Nov. 10, 2005 in the name of Tehrani et al., final Office Action mailed Jan. 31, 2011.
U.S. Appl. No. 11/981,800, filed Oct. 31, 2007 in the name of Tehrani et al., final Office Action mailed Jan. 20, 2011.
U.S. Appl. No. 10/966,421, filed Apr. 8, 2008 in the name of Tehrani, final Office Action mailed Feb. 17, 2011.
U.S. Appl. No. 11/480,074, filed Jun. 29, 2006 in the name of Tehrani et al., non-final Office Action mailed Mar. 16, 2011.
U.S. Appl. No. 10/686,891, filed Oct. 15, 2003 in the name of Tehrani, non-final Office Action mailed Mar. 30, 2011.
U.S. Appl. No. 10/966,474, filed Oct. 15, 2004 in the name of Tehrani et al., non-final Office Action mailed Mar. 30, 2011.
U.S. Appl. No. 11/981,727, filed Oct. 31, 2007 in the name of Tehrani et al., non-final Office Action mailed Apr. 4, 2011.
U.S. Appl. No. 11/249,718, filed Oct. 13, 2005 in the name of Tehrani, non-final Office Action mailed Apr. 1, 2011.
U.S. Appl. No. 11/271,726, filed Nov. 10, 2005 in the name of Tehrani et al., non-final Office Action mailed Apr. 4, 2011.
U.S. Appl. No. 11/271,264, filed Nov. 10, 2005 in the name of Tehrani et al., final Office Action mailed Apr. 7, 2011.
Heinzer, R., et al, "Lung Volume and Continuous Positive Airway Pressure Requirements in Obstructive Sleep Apeau" *American Journal of Respiratory and Critical Care Medicine*, vol. 172, pp. 114-117, 2005.
DiMarco, A F., "Combined Intercostal and Diaphragm Pacing to Provide Artificial Ventilation in Patients with Tetraplegia" *Arch Phys Med Rehabil*, vol. (86), pp. 1200-1207, 2005.
Dunn, R., "Diaphragm and Accessory Respiratory Muscle Stimulation Using Intramuscular Electrodes" *Arch Phys Med Rehabil*, vol. (76), pp. 266-271, 1995.
Glenn, W., et al. "Diaphragm Pacing" *Journal of Thoracic and Cardiovascular Surgery*, vol. (75):2, pp. 273-281, 1978.
U.S. Appl. No. 10/686,891, filed Oct. 15, 2003 in the name of Tehrani, Non-final Office Action mailed Sep. 18, 2009.
U.S. Appl. No. 11/246,439, filed Oct. 11, 2005 in the name of Tehrani, Non-final Office Action mailed Sep. 30, 2009.
U.S. Appl. No. 11/249,718, filed Oct. 13, 2005 in the name of Tehrani, Non-final Office Action mailed Apr. 18, 2008.
U.S. Appl. No. 11/249,718, filed Oct. 13, 2005 in the name of Tehrani, Final Office Action mailed Apr. 1, 2009.
U.S. Appl. No. 11/249,718, filed Oct. 13, 2005 in the name of Tehrani, Non-final Office Action mailed Nov. 25, 2009.
U.S. Appl. No. 11/981,800, filed Oct. 31, 2007 in the name of Tehrani et al., Non-final Office Action mailed Oct. 7, 2009.
U.S. Appl. No. 10/966,421, filed Oct. 15, 2004 in the name of Tehrani, Final Office Action mailed Oct. 26, 2009.
U.S. Appl. No. 11/271,554, filed Nov. 10, 2005 in the name of Tehrani et al., Non-final Office Action mailed Dec. 24, 2009.
U.S. Appl. No. 11/981,831, filed Oct. 31, 2007 in the name of Tehrani et al., Non-final Office Action mailed Jan. 6, 2010.
U.S. Appl. No. 10/966,474, filed Oct. 15, 2004 in the name of Tehrani, Final Office Action mailed Jan. 21, 2010.
U.S. Appl. No. 11/526,949, filed Sep. 25, 2006 in the name of Tehrani, Final Office Action mailed Mar. 19, 2010.
U.S. Appl. No. 11/271,726, filed Nov. 10, 2005 in the name of Tehrani et al., Non-final Office Action mailed Mar. 31, 2010.
U.S. Appl. No. 11/271,264, filed Nov. 10, 2005 in the name of Tehrani et al., Non-final Office Action mailed Mar. 30, 2010.
U.S. Appl. No. 11/271,315, filed Nov. 10, 2005 in the name of Tehrani et al., Final Office Action mailed Mar. 31, 2010.
U.S. Appl. No. 11/271,315, filed Nov. 10, 2005 in the name of Tehrani et al., Non-final Office Action mailed Oct. 3, 2008.
U.S. Appl. No. 11/981,342, filed Oct. 31, 2007 in the name of Tehrani et al., Non-final Office Action mailed Apr. 15, 2010.
U.S. Appl. No. 11/480,074, filed Jun. 29, 2006 in the name of Tehrani et al., Final Office Action mailed Apr. 30, 2010.
U.S. Appl. No. 10/966,421, filed Oct. 15, 2004 in the name of Tehrani, non-final Office Action mailed Jun. 9, 2010.
U.S. Appl. No. 12/080,133, filed Apr. 1, 2008 in the name of Tehrani et al., non-final Office Action mailed Jun. 10, 2010.
U.S. Appl. No. 11/246,439, filed Oct. 11, 2005 in the name of Tehrani, final Office Action mailed Jun. 29, 2010.
"Quadripolar Pacing Addresses Issues Without Moving Leads," *Diagnostic & Invasive Cardiology*, 1 page, Jun. 1, 2010, Scranton Gillette Communications.

Abraham, W., "Advances in Heart Failure Therapy in the Primary Care Context," *Medscape Family Medicine/Primary Care*, 7 pages, 2004.

Arzt, M. et al, "Treatment of Sleep Apnea in Heart Failure," *AJRCCM*, 36 pages, Mar. 9, 2006.

Boston Scientific, "Diaphragm Stimulation During Daily LV Lead Impedance Measurements", Product Education Brochure, 2 pages, Sep. 26, 2008.

Bradley, T.D. et al, "Sleep Apnea and Heart Failure, Part I: Obstructive Sleep Apnea," *Circulation*, pp. 1671-1678, Apr. 1, 2003.

Fessler, H.E., "Heart-Lung Interactions: Applications in the Critically Ill," *Eur. Respir. J.*, vol. 10, pp. 226-237, 1997.

Fichter, J. et al, "Sleep-Related Breathing Disorders are Associate with Ventricular Arrhythmias in Patients with an Implantable Cardioverter-Defibrillator," *Chest*, vol. 122, pp. 558-561, Aug. 2002.

Garrigue, S. et al "Sleep Apnea: A New Indication for Cardiac Pacing?," *Pace*, vol. 27, pp. 204-211, Feb. 2004.

Hayano, J. et al "Respiratory Sinus Arrhythmia: A Phenomenon Improving Pulmonary Gas Exchange and Circulatory Efficiency," *Circulation*, vol. 94, pp. 842-847, 1996.

Hennersdorf, M.G. et al, "Chemoreflexsensitivity in Chronic Heart Failure Patients," *European Journal of Heart Failure*, vol. 3, pp. 679-684, 2001.

Ishii, K. et al "Effects of Bilateral Transvenous Diaphragm Pacing on Hemodynamic Function in Patients after Cardiac Operations," *J Thorac Cardiovasc Surg.* vol. 100, pp. 108-114, 1990.

Javaheri, S. et al, "Sleep Apnea in 81 Ambulatory Male Patients with Stable Heart Failure: Types and Their Prevalences, Consequences, and Presentations," *Circulation*, vol. 97, pp. 2154-2159, 1998.

Kohnlein, T, et al, "Central Sleep Apnea Syndrome in Patients with Chronic Heart Disease: a Critical Review of the Current Literature," *Thorax*, vol. 57, pp. 547-554, 2002.

Krachman, S. et al "Comparison of Oxygen Therapy with Nasal Continuous Positive Airway Pressure on Cheyne-Stokes Respiration During Sleep in Congestive Heart Failure," *Chest*, vol. 116, pp. 1550-1557, Dec. 1999.

LaFond, C. et al "Impact of CPAP on Asthmatic Patients with Obstructive Sleep Apnoea," *Eur Respir J*, vol. 29. pp. 307-311, 2007.

Lanfranchi, P.A. et al, "Prognostic Value of Nocturnal Cheyne-Stokes Respiration in Chronic Heart Failure," *Circulation*, pp. 1435-1440, 1999.

Leung, R. et al, "Sleep Apnea and Cardiovascular Disease," *Am J Respir Crit Care Med*, vol. 164, pp. 2147-2165, 2001.

Mathew, O., "Effects of Transient Intrathoracic Pressure Changes (hiccups) on Systemic Arterial Pressure," *J Appl Physiol*, vol. 83, pp. 371-375, 1997.

Norton, J., "Toward Consistent Definitions for Preload and Afterload," *Advan in Physiol Edu*, vol. 25, pp. 53-61, Mar. 2001.

Peters, J. et al, "Negative Intrathoracic Pressue Decreases Independently Left Ventricular Filling and Emptying," *American Physiological Society*, pp. H120-H131, 1989.

Pinsky, M. "Cardiovascular Issues in Respiratory Care," *Chest*, vol. 128, pp. 592-597, Nov. 2005.

Schultz, R. et al "Nocturnal Periodic Breathing in Primary Pulmonary Hypertension," *Eur Respir J*, vol. 19, pp. 658-663, 2002.

Series, T. et al, "Assessment of Upper Airway Stabilizing Forces with the Use of Phrenic Nerve Stimulation in Conscious Humans," *J Appl Physiol*, vol. 94, pp. 2289-2295, 2003.

Sorli, J. et al., "Ventilatory Assist Using Electrical Stimulation of AJdominal Muscles," *IEEE Transactions of Rehabilitation Engineering*, vol. 4. No. 1, pp. 1-6, Mar. 1996.

Van Houwelingen, K. et al "The Sleep Apnoea Syndromes," *European Heart Journal*, vol. 20. pp. 858-866, Jun. 1999.

Viasys Healthcare, "Ventilation Requires Perfect Balance", SensorMedics® 3100A HFOV, VIASYS Healthcare Brochure, 2 pages.

Wolk, R. et al "Sleep-Disordered Breathing and Cardiovascular Disease," *Circulation*, vol. 108, pp. 9-12, Jul. 2003.

Yim, S. et al "Continuous Positive Airway Pressure for Asthma: Not a Big Stretch?," *Eur Respir J*, vol. 29, pp. 226-228, 2007.

F. Series, et al., "Increasing the Functional Residual Capacity May Reverse Obstructive Sleep Apnea Sleep" 11(4); 349-353 (1988).

* cited by examiner

| Respiratory Rate (RR) | $RR_d$ | $RR_n$ | $RR_i$ |
|---|---|---|---|
| Decrease X% Increase Y% | (1-X/100)*Observed | Observed | (1+Y/100)*Observed |

*FIG. 2*

| Tidal Volume | Respiratory Rate (RR) | Inspiration Duration (ID) |
|---|---|---|
| Normal | $RR_d$ | $ID_d$ |
| Normal | $RR_n$ | $ID_n$ |
| Normal | $RR_i$ | $ID_i$ |

*FIG. 3*

|  | Tidal Volume (10-30%) | Respiratory Rate (30-50%) |
|---|---|---|
| Increase / Decrease |  |  |

*FIG. 5*

Minute Ventilation Changes

| Respiratory Rate | Inspiration Duration | Tidal Volume | | |
|---|---|---|---|---|
|  |  | Decreased | Normal | Increased |
| $RR_d$ | $ID_d$ | ↓ | ↓ | ↓ |
| $RR_n$ | $ID_n$ | ↓ | — | ↑ |
| $RR_i$ | $ID_i$ | ↓ ↑ | ↑ | ↑ |

*FIG. 6*

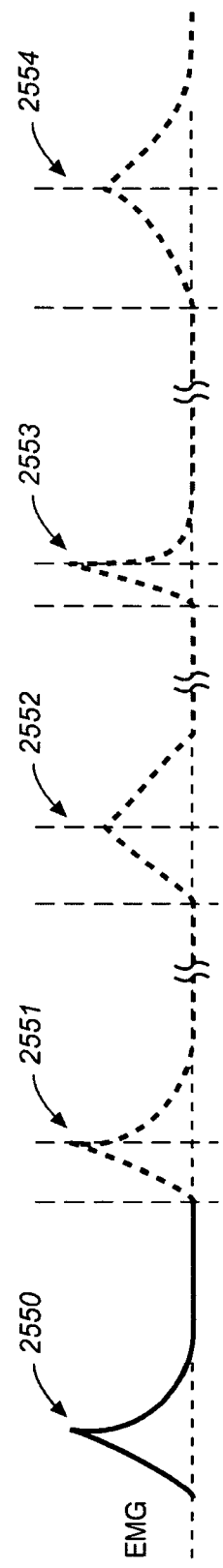
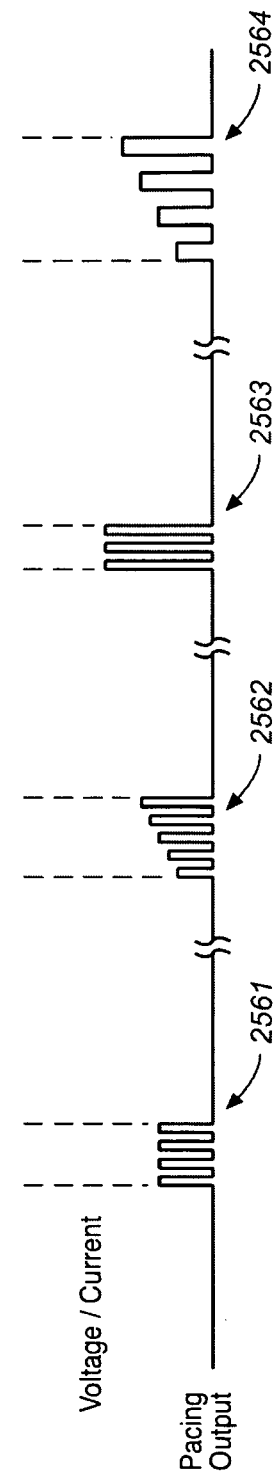
FIG. 25A
FIG. 25B

SYSTEM AND METHOD FOR DIAPHRAGM STIMULATION

RELATED APPLICATION DATA

This application is related to U.S. patent application Ser. No. 10/686,891, "BREATHING DISORDER DETECTION AND THERAPY DELIVERY DEVICE AND METHOD", by Tehrani et al., filed Oct. 15, 2003, and incorporated herein by reference.

FIELD OF THE INVENTION

The present invention relates to devices, systems, and methods useful for providing ventilation through stimulation of the diaphragm.

BACKGROUND OF THE INVENTION

The human body's ability to maintain homeostasis is due in part due to respiratory functions controlled by the brain and associated feedback systems. In maintaining homeostasis, respiratory functions typically alter both blood oxygen saturation and carbon dioxide partial pressures.

Certain pathological conditions such as circulation delay in heart failure patients may lead to instability in the respiratory feedback systems. Circulatory delay is believed to cause phase shift or time delay in the inherent blood gas sensing feedback loop. One manifestation of this is resulting breathing disorders including periodic breathing, Cheyne-Stokes, and apnea (predominantly central sleep apnea (CSA)). Cheyne-Stokes respiration is believed to occur in part because of this circulatory delay and perceived drop in $SaO_2$ levels. Central apnea, and, in some cases obstructive apnea, is believed to occur in part due to a drop in partial pressure of $CO_2$ following a Cheyne-Stokes hyperventilation pattern. Other conditions such as congestive heart failure (CHF) may be able to derive a benefit by an increase in the partial pressure of $O_2$ above that which is normally maintained.

Mechanical ventilators have been used to take over breathing to ensure adequate oxygen levels in patients who cannot sufficiently breath on their own or who stop breathing at night during apnea events. Mechanical ventilators control the inflow and egress of respiratory gasses by controlling combinations of flow, pressure and/or volume. The ventilator delivers an inspiration via positive pressure delivered into the trachea and lungs and can control exhalation by manipulating pressure and flow.

Diaphragm stimulation has been used to create respiration in patients who cannot breath on their own and has been suggested to stimulate breathing when apnea occurs. Diaphragmatic stimulation has generally been used to control inspiration via contraction of the diaphragm muscle which creates negative intra-thoracic pressure resulting in inspiration. Exhalation has generally been a passive process driven by lung and thoracic compliance.

The ventilators and proposed diaphragm stimulation have not addressed the causes of breathing disorders, but rather have been limited to supplementing breathing when breathing is insufficient or not present.

BRIEF SUMMARY OF THE INVENTION

The present invention provides an implantable device for delivering electrical stimulation waveforms to the diaphragm through one or more electrodes. In particular, one aspect of the invention provides stimulation waveforms that are directed to manipulation of patient blood gases, e.g., $SaO_2$ and $PCO_2$. In order to achieve manipulation of blood gas concentration, in one embodiment minute ventilation is increased or decreased with respect to a baseline minute ventilation. This may be done by manipulation of one or more parameters affecting minute ventilation. Some of the parameters may include, for example, tidal volume, respiration rate, flow morphology, flow rate, inspiration duration, slope of the inspiration curve, and diaphragm-created or intrathoracic pressure gradients. The implantable device may be programmed by a programmer that is coupled to a flow sensor that measures the natural respiration and stimulation respiration of a subject. Normal breathing of a patient is observed to establish a baseline reference minute ventilation, and the device is programmed to produce stimulation waveforms that may provide either a decrease or an increase in the patients minute ventilation.

In one embodiment of the invention the reference minute ventilation of a patient is obtained by observing normal breathing of a patient in an awake state, and increased and decreased minute ventilation are obtained by interacting with the patient.

In another embodiment the reference minute ventilation of a patient is obtained by observing the patient in the sleeping state, and increased and decreased minute ventilation are obtained by applying a predetermined multiplier.

In yet another embodiment the minute ventilation is decreased from the reference level by decreasing one or more of the following parameters: respiratory rate, inspiration duration, and tidal volume.

In still another embodiment the minute ventilation is increased from the reference level by increasing one or more of the following parameters: respiratory rate, inspiration duration, and tidal volume.

In a further embodiment an electrical stimulation waveform is provided for creating an enhanced negative intrapleural pressure during exhalation.

BRIEF DESCRIPTION OF THE DRAWINGS

FIG. 2 shows a parameter table for selected respiratory rates in accordance with the invention.

FIG. 3 shows a parameter table for measured inspiration duration in accordance with the invention.

FIG. 5 shows a parameter table for diaphragm stimulation parameters in accordance with the invention.

FIG. 6 shows a parameter table of the respiratory changes associated with stimulation combinations in accordance with the invention.

FIG. 24B is a flow diagram of sleep apnea treatment with a stimulator in accordance with the invention.

FIG. 24C is a flow diagram of hypoventilation treatment with a stimulator in accordance with the invention.

FIG. 24D is a flow diagram of hyperventilation treatment with a stimulator in accordance with the invention.

FIGS. 25A-25B are an illustration of a variety of stimulation bursts with different parameters (FIG. 25B) corresponding to different resulting EMG signals (FIG. 25A).

DETAILED DESCRIPTION OF THE INVENTION

Figure 1:
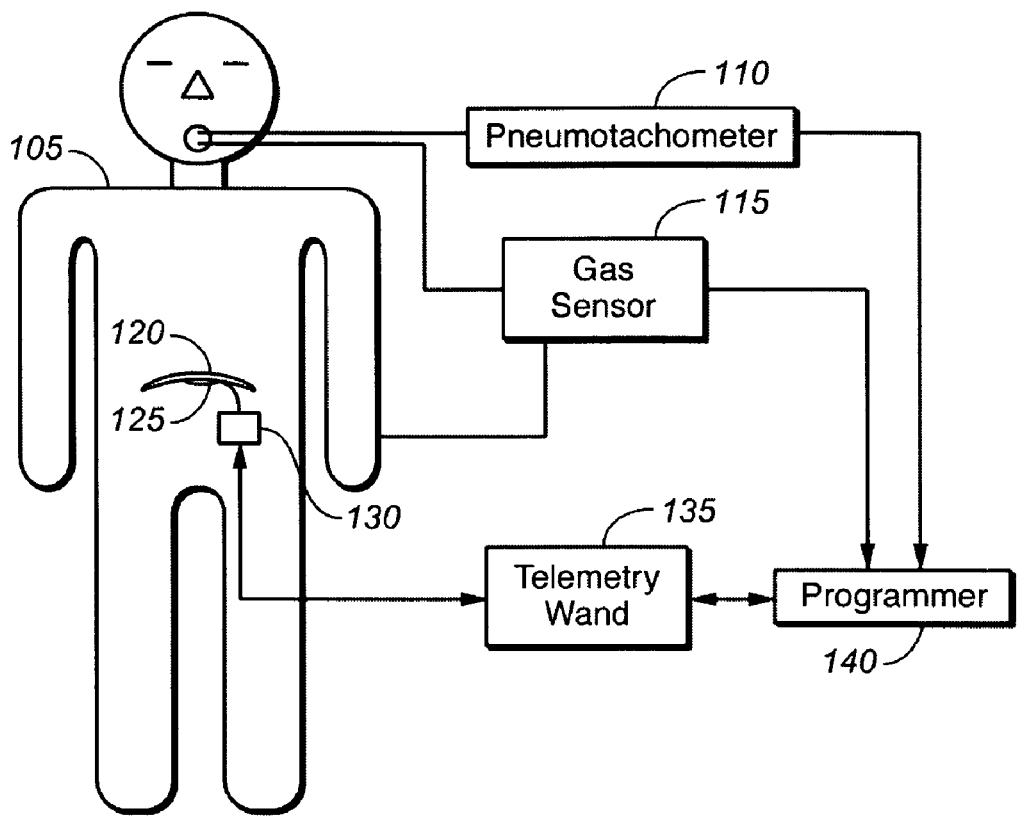
FIG. 1 shows a diagram of a diaphragm stimulator device in accordance with the present invention.

FIG. 1 shows a diagram of a system 100 for diaphragm stimulation in accordance with the invention. A subject 105 is implanted with a programmable stimulation device 130 that is coupled to one or more electrodes 125 in contact with the diaphragm 120. The one or more electrodes 125 may include both sensing and stimulation electrodes. A flow measuring device 110 (e.g., a pneumotachometer) is used to measure the respiratory flow characteristics (e.g., tidal volume, inspiration duration, and respiratory rate) of the subject 105.

A programmer 140 is coupled to the flow measuring device 110. The programmer 140 is also coupled to the implanted programmable stimulating device 130 by a telemetry wand 135. An optional sensor 115 may also be coupled to the subject 105 and to the programmer for collecting respiratory and/or blood gas composition data (e.g., pulse oximetry or exhaled gas composition).

The system 100 may be used to determine a minute ventilation baseline reference value for a subject and the device 130 may be programmed to provide a waveform stimulus to adjust the minute ventilation of the subject about the baseline reference value. Minute ventilation is the tidal volume x respiration rate for a minute of time. Minute ventilation may be determined by an ensuing tidal volume over time or an instantaneous value. The minute ventilation of the subject generally increases or decreases with increase or decrease in energy (e.g., in frequency, current, pulse width, or amplitude) applied to the diaphragm. The energy applied by the device 130 may be adjusted by selection of the amplitude, frequency, pulse width, and duration of the series of pulses or stimulus waveform applied by the device 130.

The device may be programmed to produce stimulation waveforms that vary the combination of respiratory rate and tidal volume which result in an increase or decrease of minute ventilation from a reference level. Increasing minute ventilation generally increases the partial pressure of $O_2$ compared to a reference minute ventilation. Decreasing minute ventilation generally increases the partial pressure of $CO_2$ compared to a reference minute ventilation. Accordingly, the invention provides a method and device that manipulates blood gas concentration.

The system shown in diagram 100 may be used to observe the natural normal, or intrinsic respiration of a subject in either the waking state or the sleeping state. When the flow measuring device 110 is a pneumotachometer, the subject will more likely be in the waking state.

The device 130 may be programmed to provide stimulation assistance that is correlated with normal respiration rate ($RR_n$), decreased respiration rate ($RR_d$), or increased respiration rate ($RR_i$). FIG. 2 shows a parameter table for selecting respiratory rates in accordance with an embodiment of the present invention. The value for $RR_d$ is selected as a fixed percentage (100−X) of the observed normal respiratory rate of the subject. Similarly, The value for $RR_i$ is selected as a fixed percentage (100+Y) of the observed normal respiratory rate of the subject. Although X and Y are not required to be equal, for simplicity they are set equal in the discussion that follows.

FIG. 3 shows a parameter table for measured inspiration duration in accordance with an embodiment of the present invention. Typically, inspiration duration is not constant and will vary inversely with the respiration rate. Thus, a decreased inspiration duration $ID_d$ is associated with an increased respiratory rate $RR_d$, and an increased inspiration duration $ID_i$ is associated with a decreased respiratory rate $RR_d$. In order to establish the duration of the stimulus waveform for a constant tidal volume, the subject's inspiration duration is measured while breathing at the selected breathing rates. In this example, the target tidal volume is the same as the observed normal tidal volume value.

For stimulation therapy that is to be delivered while a patient is sleeping, the most accurate baseline respiratory rate and tidal volume are those that are observed while the subject is asleep. However, since monitoring of a sleeping subject may not provide the required respiratory rates at the normal tidal volume, a waking subject may be coached to provide the required tidal volume and respiratory rate combinations so that the associated inspiration duration can be measured. A clinician will typically allow a period of time for the subject to be relaxed. Alternatively, hypnosis or meditative techniques may used to place the subject in a suitable state. In order to obtain defined parameter values an average over two or more inspiration/exhalation cycles may be taken.

Figure 4:
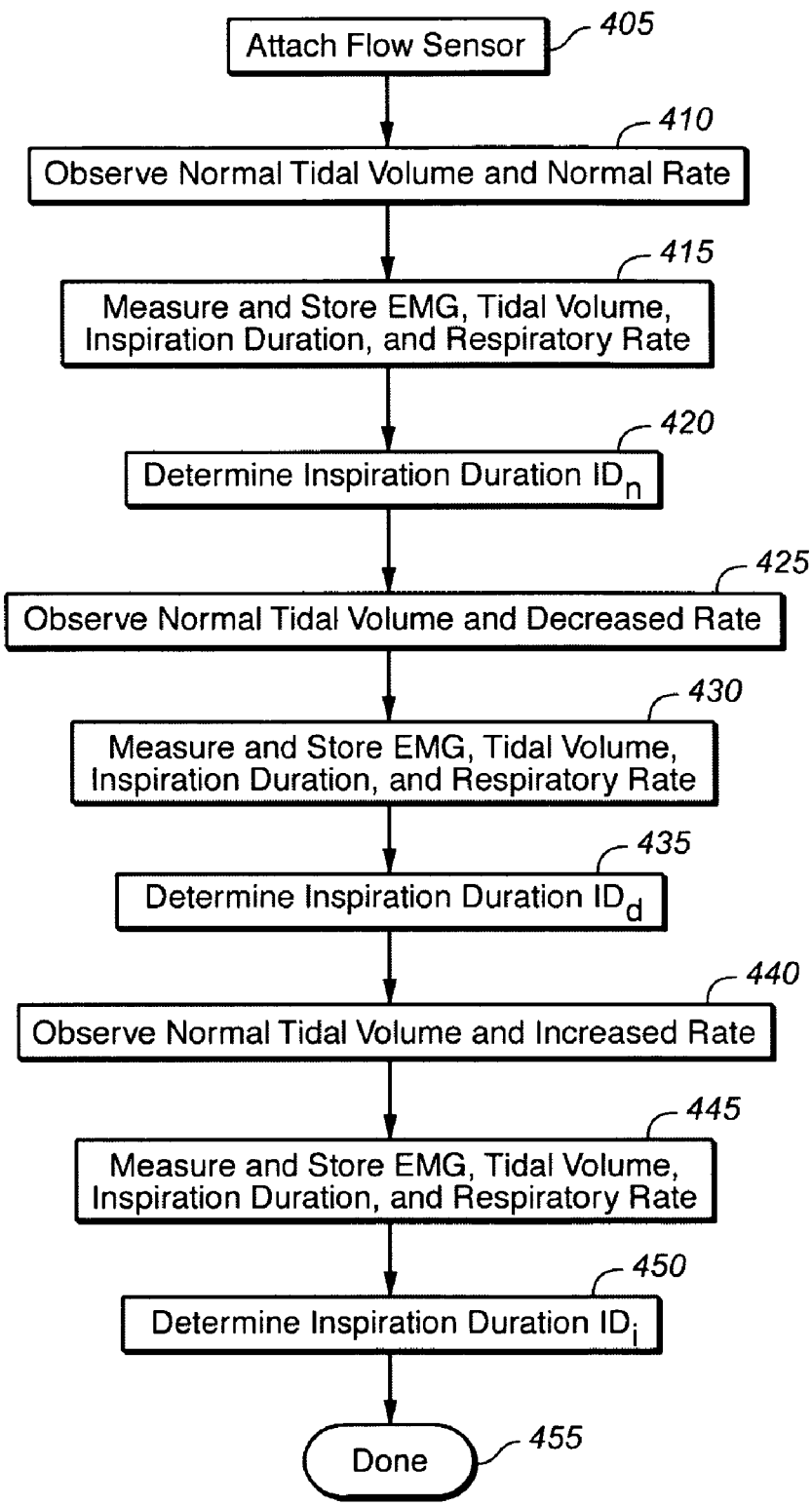
FIG. 4 shows a flow diagram for establishing a baseline respiratory reference in accordance with the invention.

FIG. 4 shows a flow diagram for establishing a baseline respiratory reference for a subject in accordance with a method embodiment of the present invention. In step 405 a flow sensor (e.g., a pneumotachometer) is attached to the subject. In step 410 the normal tidal volume and normal respiration rate are observed. In step 415, when the subject is in a satisfactory state, the electromyogram (EMG) of the diaphragm, tidal volume, and inspiration duration are measured and recorded. In step 420 the normal inspiration duration $ID_n$ is determined. The value for $ID_n$ may be an average of selected observed values (e.g., a moving average).

In step 425 a decreased respiration rate at the normal tidal volume is observed. In step 430 the electromyogram (EMG) of the diaphragm, tidal volume, and inspiration duration are measured and recorded. The subject may be breathing spontaneously or may be coached. In step 435 the decreased inspiration duration $ID_d$ is determined. The value for $ID_d$ may be an average of selected observed values (e.g., a moving average).

In step 440 an increased respiration rate at the normal tidal volume is observed. In step 445 the electromyogram (EMG) of the diaphragm, tidal volume, and inspiration duration are measured and recorded. The subject may be breathing spontaneously or may be coached. In step 450 the increased inspiration duration $ID_i$ is determined. The value for $ID_i$ may be an average of selected observed values (e.g., a moving average). At step 455 the baseline reference determination is complete. While the $ID_d$ and $ID_i$ may be measured as noted, they also may be calculated based on the $ID_n$, for example, as a percentage change from the $ID_n$.

FIG. 5 shows a parameter selection table for diaphragm stimulation parameters in accordance with an embodiment of the present invention. Diaphragm stimulation may be used to adjust minute ventilation by varying the tidal volume and/or respiratory rate. The preferred range for the change in tidal volume from normal is 10-30% of normal and the preferred range for the change in respiratory rate from normal is 30-50%.

When applying stimulus waveforms between cycles in a subject's spontaneous breathing pattern, the inspiration duration must be correlated with the subject's respiratory rate. Thus, although the tidal volume may be adjusted through adjustments in inspiration duration, it is preferable to adjust the tidal volume by adjusting the frequency and amplitude of the stimulus waveform.

FIG. 6 shows a parameter table of the minute ventilation changes associated with stimulation combinations in accordance with an embodiment of the present invention. The table in FIG. 6 is a 3×3 matrix of minute ventilation that is the product of respiratory rate (at a given inspiration duration) and tidal volume. The up and down arrows in the matrix of the table in FIG. 6 correspond to a respective increase or decrease in minute ventilation in relation to the minute ventilation for normal tidal volume and $RR_n/ID_n$. For example, the combination of $RR_d/ID_d$ and decreased tidal volume result in a decrease in minute ventilation, and the combination of $RR_i/ID_i$ and increased tidal volume produce an increase in minute ventilation. These results are consistent regardless of the percent change selected for tidal volume and respiratory rate within the preferred ranges shown in FIG. 5.

It should be noted that the combination of $RR_i/ID_i$ and decreased tidal volume may produce either an increase or decrease in minute ventilation, depending upon the values selected for percent change in tidal volume and respiratory rate. The discrete values in the table of FIG. 6 may be used to provide limits for continuously variable parameters. Continuous parameter functions may be obtained by interpolation of discrete values.

Figure 7:
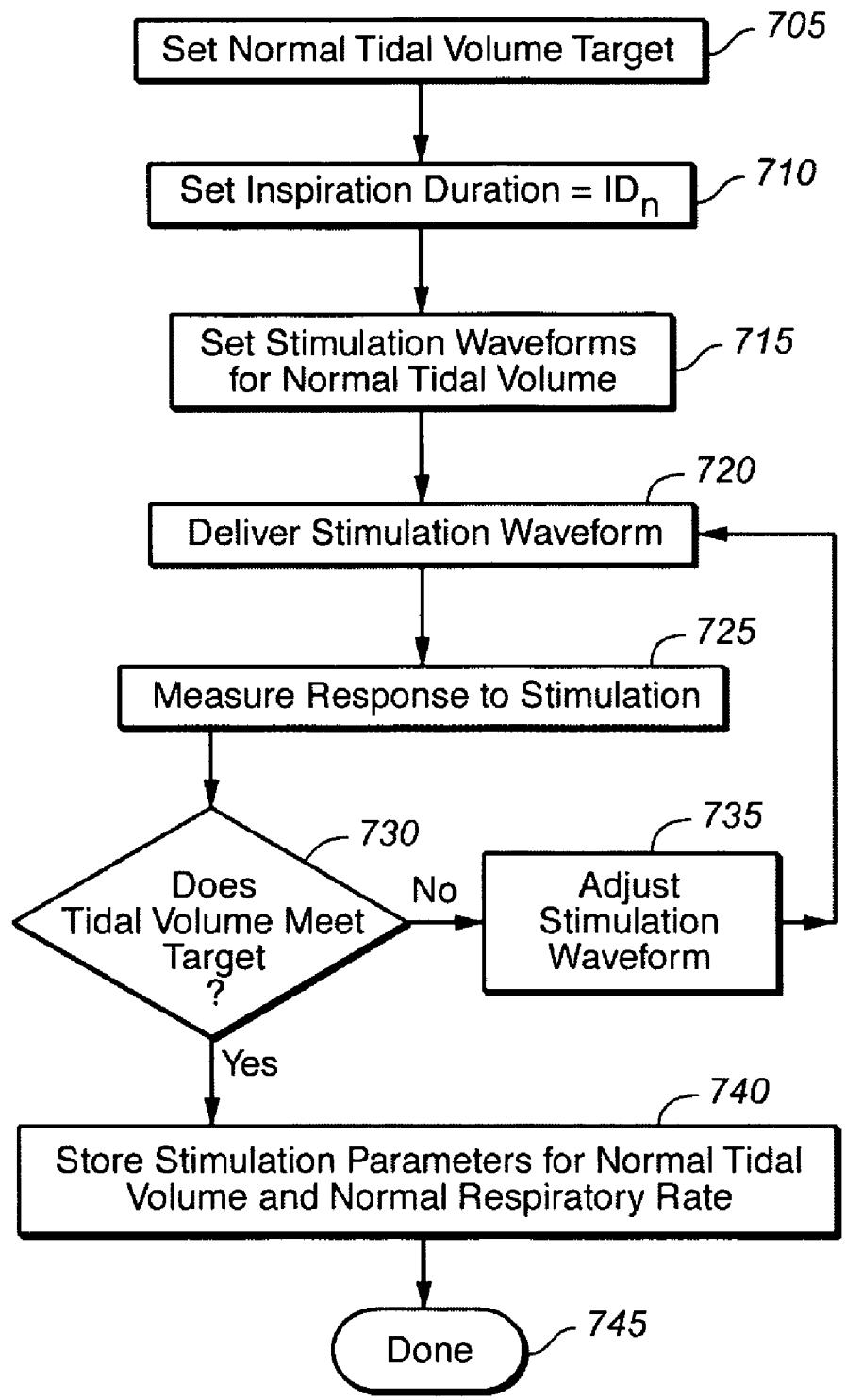
FIG. 7 shows a flow diagram for establishing stimulation waveforms with a normal tidal volume and a normal respiratory rate in accordance with the invention.

FIG. 7 shows a flow diagram for establishing stimulation waveforms with a normal tidal volume and a normal respiratory rate in accordance with a method embodiment of the present invention. In step 705 the observed normal tidal value is selected as a target. In step 710 the waveform inspiration duration is set to the $ID_n$ associated with the normal respiratory rate.

In step 715 the stimulation waveforms are given initial amplitude and frequency values, and initial amplitude and frequency ramp value variations (i.e., increases in amplitude and/or frequency during a stimulation burst or series of pulses. These values are selected to produce the observed normal tidal volume. The values may be selected on the basis of information specific to the subject such as previously observed mapping data. A discussion of diaphragm mapping and stimulus waveforms may be found in application Ser. No. 10/686,891, "BREATHING DISORDER DETECTION AND THERAPY DELIVERY DEVICE AND METHOD", by Tehrani et al., filed Oct. 15, 2003, and incorporated herein by reference, and in related U.S. patent application entitled "SYSTEM AND METHOD FOR MAPPING DIAPHRAGM ELECTRODE SITES" filed on even date herewith.

In step 720 the stimulation waveform is delivered to the diaphragm. In step 725 the response to the stimulation waveform is measured. In step 730 a criterion for accepting the response is evaluated. For example, the measured response tidal volume must be within a fixed percentage (e.g., 5%) of the target tidal volume of step 705. If the criterion is not met step 735 is executed. In step 735 the stimulation waveform is adjusted. If the criterion is met in step 730, step 740 is executed. In step 740 the waveform parameters are stored for normal tidal volume at normal respiratory rate. In step 745 the stimulation waveform parameters are established.

Figure 8:
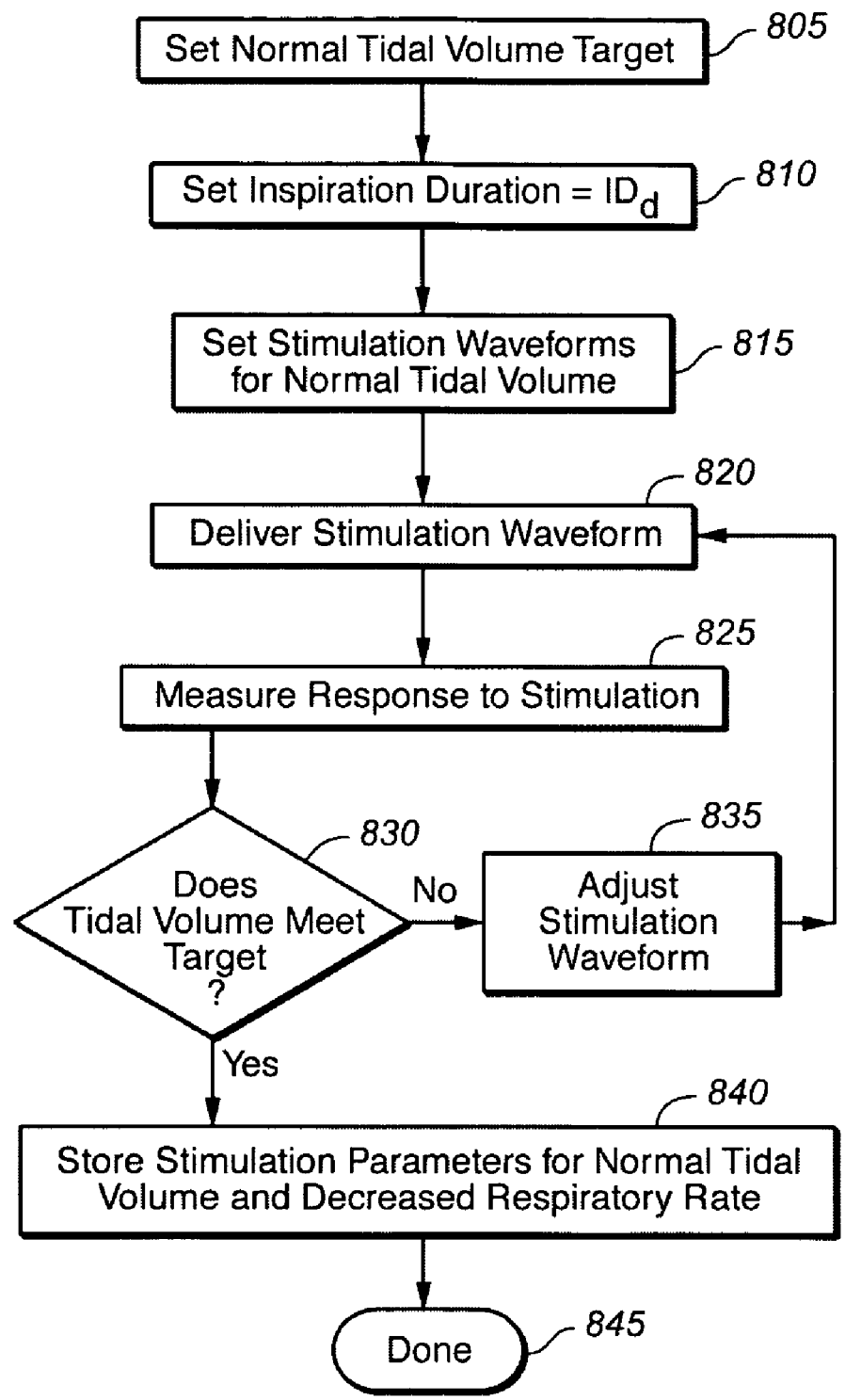
FIG. 8 shows a flow diagram for establishing stimulation waveforms with a normal tidal volume and a decreased respiratory rate in accordance with the invention.

FIG. 8 shows a flow diagram for establishing stimulation waveforms with a normal tidal volume and a decreased respiratory rate in accordance with a method embodiment of the present invention. In step 805 the observed normal tidal value is selected as a target. In step 810 the waveform inspiration duration is set to the $ID_d$ associated with the decreased respiratory rate for example, as determined herein with reference to FIG. 2 or 3.

In step 815 the stimulation waveforms are given initial amplitude and frequency values, and initial amplitude and frequency ramp values. These values are selected to produce the observed normal tidal volume. The values may be selected on the basis of information specific to the subject such as previously observed mapping data.

In step 820 the stimulation waveform is delivered to the diaphragm. In step 825 the response to the stimulation waveform is measured. In step 830 a criterion for accepting the response is evaluated. For example, the measured response tidal volume must be within a fixed percentage (e.g., 5%) of the target tidal volume of step 805. If the criterion is not met step 835 is executed. In step 835 the stimulation waveform is adjusted. If the criterion is met in step 830, step 840 is executed. In step 840 the waveform parameters are stored for normal tidal volume at decreased respiratory rate. In step 845 the stimulation waveform parameters are established.

Figure 9:
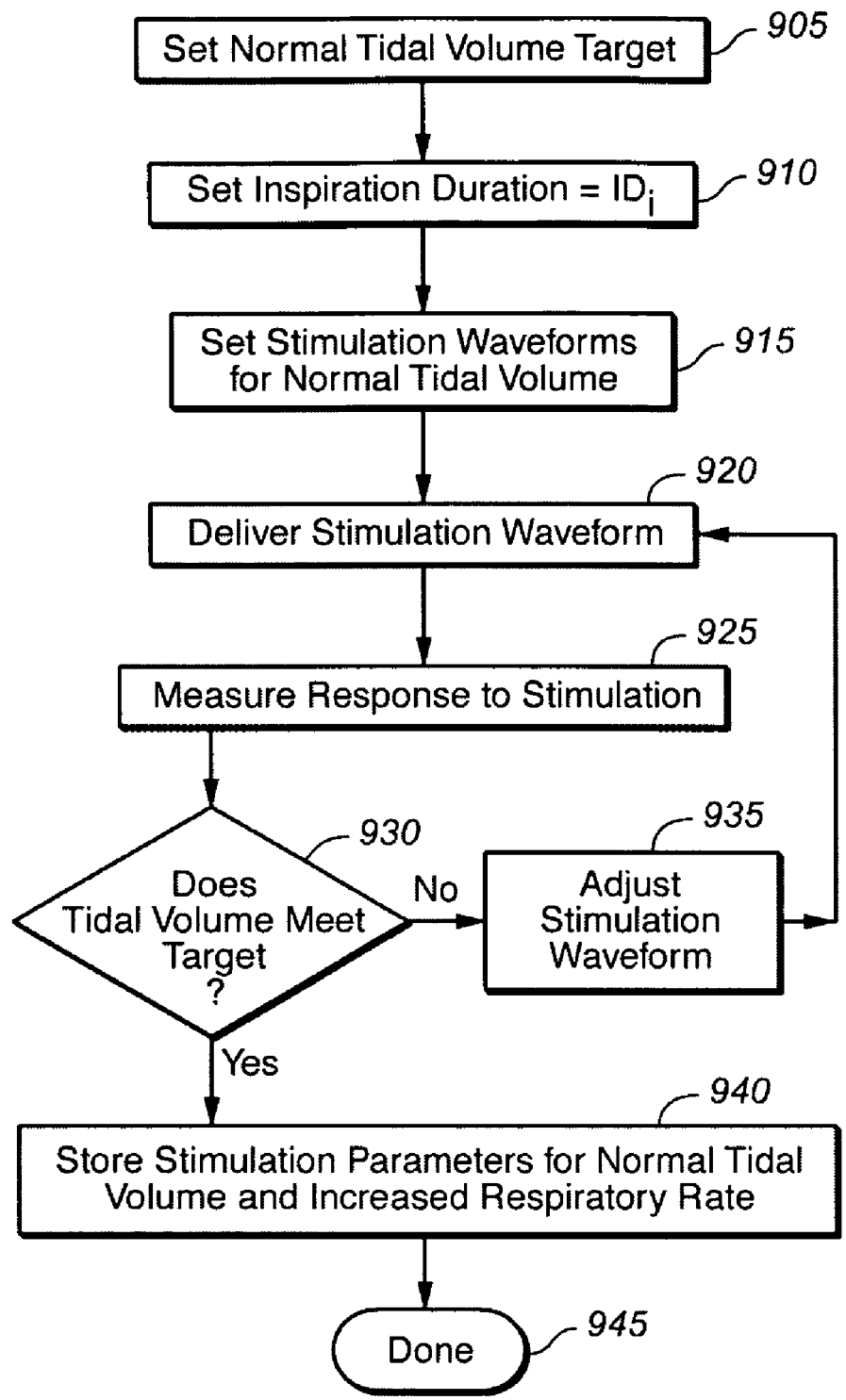
FIG. 9 shows a flow diagram for establishing stimulation waveforms with a normal tidal volume and an increased respiratory rate in accordance with the invention.

FIG. 9 shows a flow diagram for establishing stimulation waveforms with a normal tidal volume and an increased respiratory rate in accordance with a method embodiment of the present invention. In step 905 the observed normal tidal value is selected as a target. In step 910 the waveform inspiration duration is set to the $ID_i$ associated with the increased respiratory rate.

In step 915 the stimulation waveforms are given initial amplitude and frequency values, and initial amplitude and frequency ramp values. These values are selected to produce the observed normal tidal volume. The values may be selected on the basis of information specific to the subject such as previously observed mapping data.

In step 920 the stimulation waveform is delivered to the diaphragm. In step 925 the response to the stimulation waveform is measured. In step 930 a criterion for accepting the response is evaluated. For example, the measured response tidal volume must be within a fixed percentage (e.g., 5%) of the target tidal volume of step 905. If the criterion is not met step 935 is executed. In step 935 the stimulation waveform is adjusted. If the criterion is met in step 930, step 940 is executed. In step 940 the waveform parameters are stored for normal tidal volume at increased respiratory rate. In step 945 the stimulation waveform parameters are established.

Figure 10:
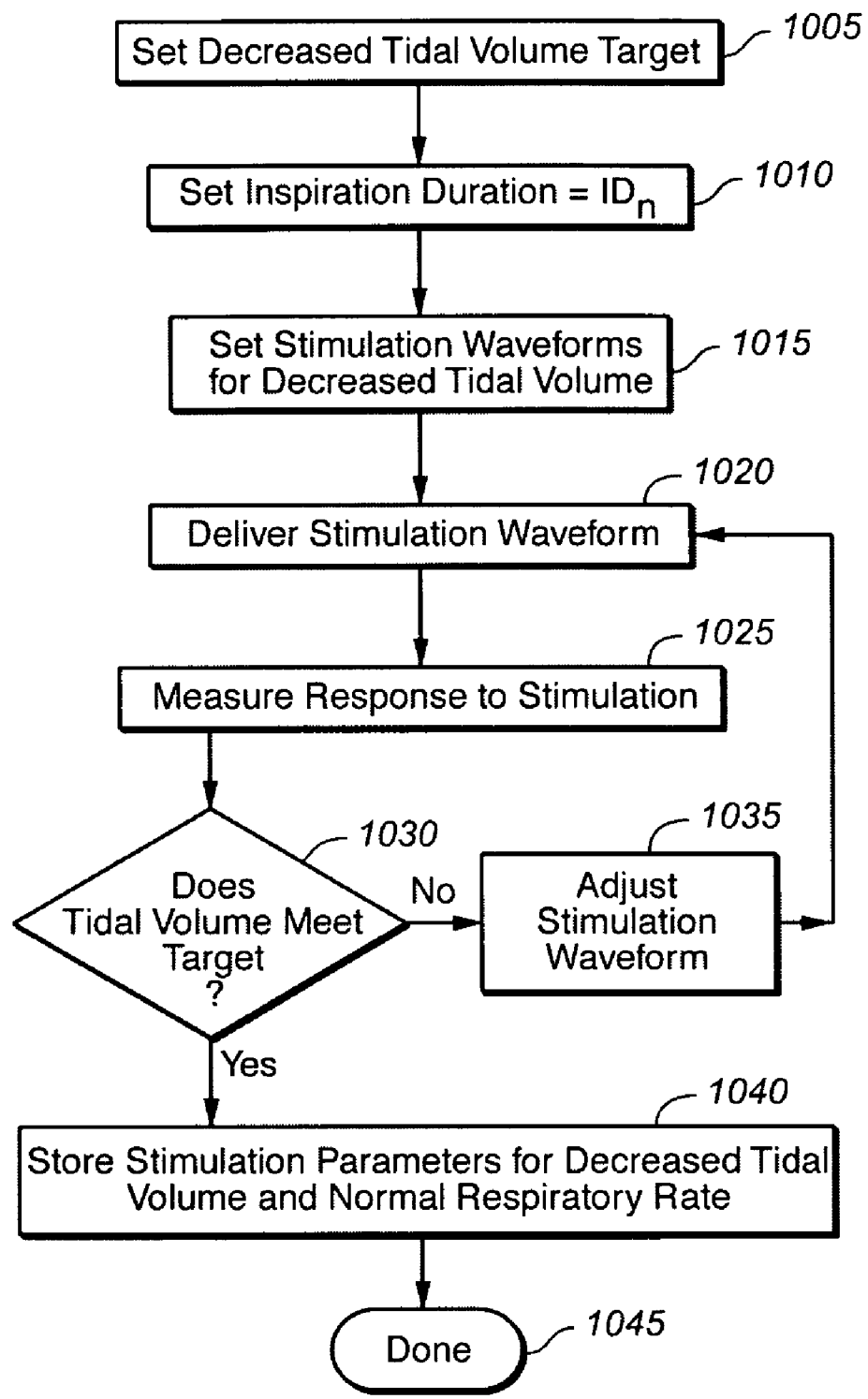
FIG. 10 shows a flow diagram for establishing stimulation waveforms with a decreased tidal volume and a normal respiratory rate in accordance with the invention.

FIG. 10 shows a flow diagram for establishing stimulation waveforms with a decreased tidal volume and a normal respiratory rate in accordance with a method embodiment of the present invention. In step 1005 the observed decreased tidal value is selected as a target. In step 1010 the waveform inspiration duration is set to the $ID_n$ associated with the normal respiratory rate.

In step 1015 the stimulation waveforms are given initial amplitude and frequency values, and initial amplitude and frequency ramp values. These values are selected to produce the selected decreased tidal volume. The values may be selected on the basis of information specific to the subject such as previously observed mapping data.

In step 1020 the stimulation waveform is delivered to the diaphragm. In step 1025 the response to the stimulation waveform is measured. In step 1030 a criterion for accepting the response is evaluated. For example, the measured response tidal volume must be within a fixed percentage (e.g., 5%) of the target tidal volume of step 1005. If the criterion is not met step 1035 is executed. In step 1035 the stimulation waveform is adjusted. If the criterion is met in step 1030, step 1040 is executed. In step 1040 the waveform parameters are stored for decreased tidal volume at normal respiratory rate. In step 1045 the stimulation waveform parameters are established.

Figure 11:
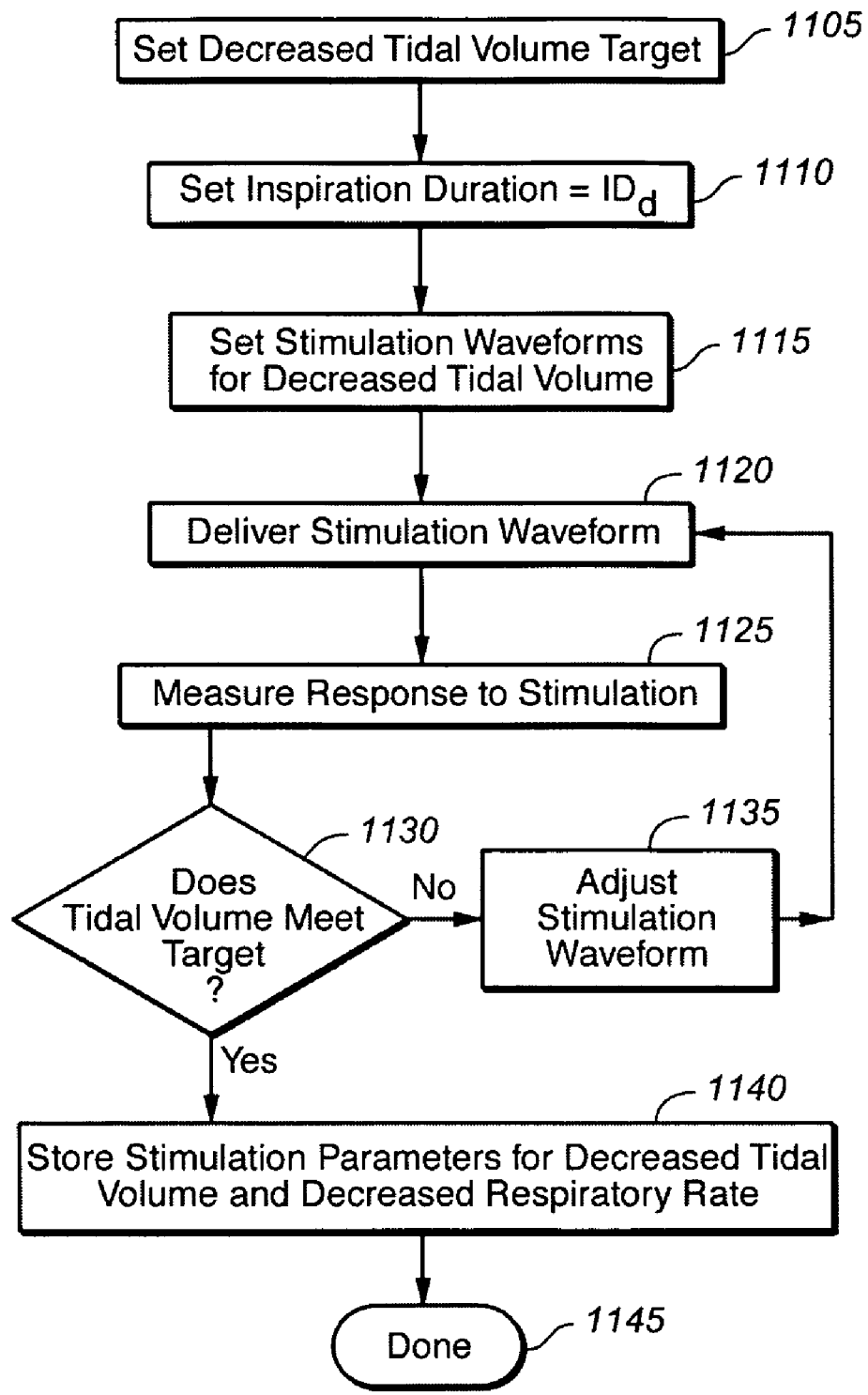
FIG. 11 shows a flow diagram for establishing stimulation waveforms with a decreased tidal volume and a decreased respiratory rate in accordance with the invention.

FIG. 11 shows a flow diagram for establishing stimulation waveforms with a decreased tidal volume and a decreased respiratory rate in accordance with a method embodiment of the present invention. In step 1105 the observed decreased tidal value is selected as a target. In step 1110 the waveform inspiration duration is set to the $ID_d$ associated with the decreased respiratory rate.

In step 1115 the stimulation waveforms are given initial amplitude and frequency values, and initial amplitude and frequency ramp values. These values are selected to produce the selected decreased tidal volume. The values may be selected on the basis of information specific to the subject such as previously observed mapping data.

In step 1120 the stimulation waveform is delivered to the diaphragm. In step 1125 the response to the stimulation waveform is measured. In step 1130 a criterion for accepting the response is evaluated. For example, the measured response tidal volume must be within a fixed percentage (e.g., 5%) of the target tidal volume of step 1105. If the criterion is not met step 1135 is executed. In step 1135 the stimulation waveform is adjusted. If the criterion is met in step 1130, step 1140 is executed. In step 1140 the waveform parameters are stored for decreased tidal volume at decreased respiratory rate. In step 1145 the stimulation waveform parameters are established.

Figure 12:
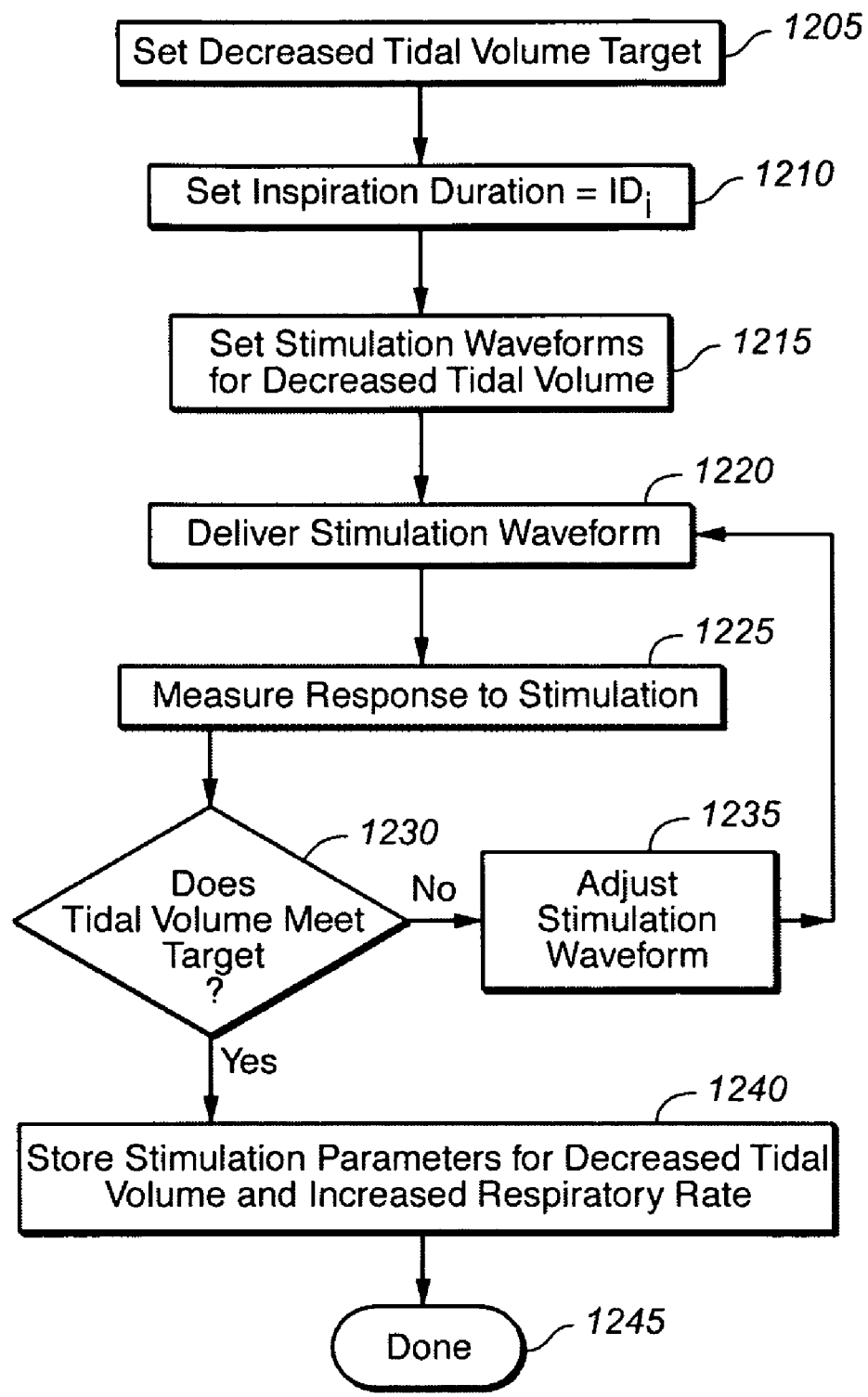
FIG. 12 shows a flow diagram for establishing stimulation waveforms with a decreased tidal volume and an increased respiratory rate in accordance with the invention.

FIG. 12 shows a flow diagram for establishing stimulation waveforms with a decreased tidal volume and an increased respiratory rate in accordance with a method embodiment of the present invention. In step 1205 the observed decreased tidal value is selected as a target. In step 1210 the waveform inspiration duration is set to the $ID_i$ associated with the increased respiratory rate.

In step 1215 the stimulation waveforms are given initial amplitude and frequency values, and initial amplitude and frequency ramp values. These values are selected to produce the selected decreased tidal volume. The values may be selected on the basis of information specific to the subject such as previously observed mapping data.

In step 1220 the stimulation waveform is delivered to the diaphragm. In step 1225 the response to the stimulation waveform is measured. In step 1230 a criterion for accepting the response is evaluated. For example, the measured response tidal volume must be within a fixed percentage (e.g., 5%) of the target tidal volume of step 1205. If the criterion is not met step 1235 is executed. In step 1235 the stimulation waveform is adjusted. If the criterion is met in step 1230, step 1240 is executed. In step 1240 the waveform parameters are stored for decreased tidal volume at increased respiratory rate. In step 1245 the stimulation waveform parameters are established.

Figure 13:
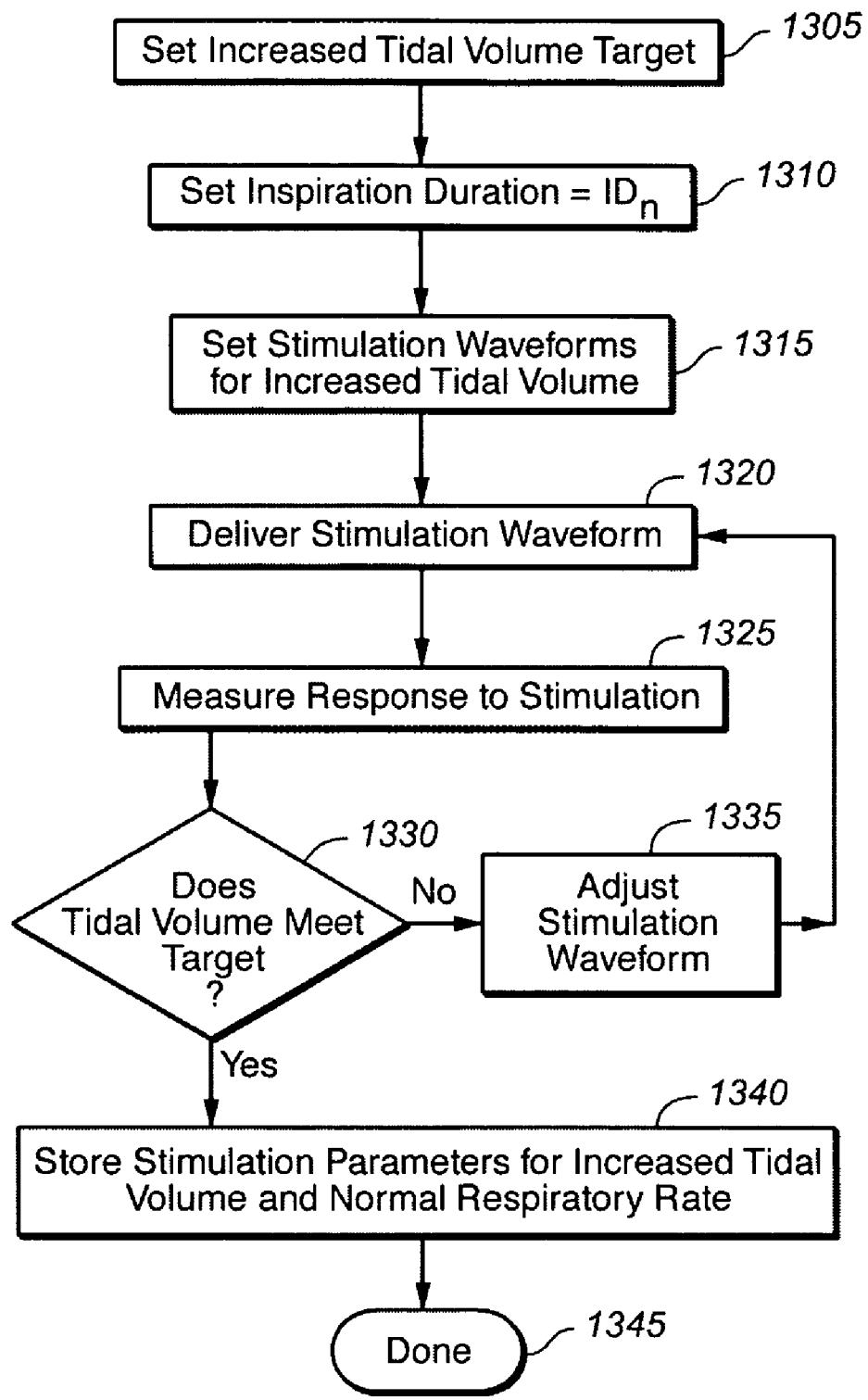
FIG. 13 shows a flow diagram for establishing stimulation waveforms with an increased tidal volume and a normal respiratory rate in accordance with the invention.

FIG. 13 shows a flow diagram for establishing stimulation waveforms with an increased tidal volume and a normal respiratory rate in accordance with a method embodiment of the present invention. In step 1305 the selected increased tidal value is selected as a target. In step 1310 the waveform inspiration duration is set to the $ID_n$ associated with the normal respiratory rate.

In step 1315 the stimulation waveforms are given initial amplitude and frequency values, and initial amplitude and frequency ramp values. These values are selected to produce the selected increased tidal volume. The values may be selected on the basis of information specific to the subject such as previously observed mapping data.

In step 1320 the stimulation waveform is delivered to the diaphragm. In step 1325 the response to the stimulation waveform is measured. In step 1330 a criterion for accepting the response is evaluated. For example, the measured response tidal volume must be within a fixed percentage (e.g., 5%) of the target tidal volume of step 1305. If the criterion is not met step 1335 is executed. In step 1335 the stimulation waveform is adjusted. If the criterion is met in step 1330, step 1340 is executed. In step 1340 the waveform parameters are stored for increased tidal volume at normal respiratory rate. In step 1345 the stimulation waveform parameters are established.

Figure 14:
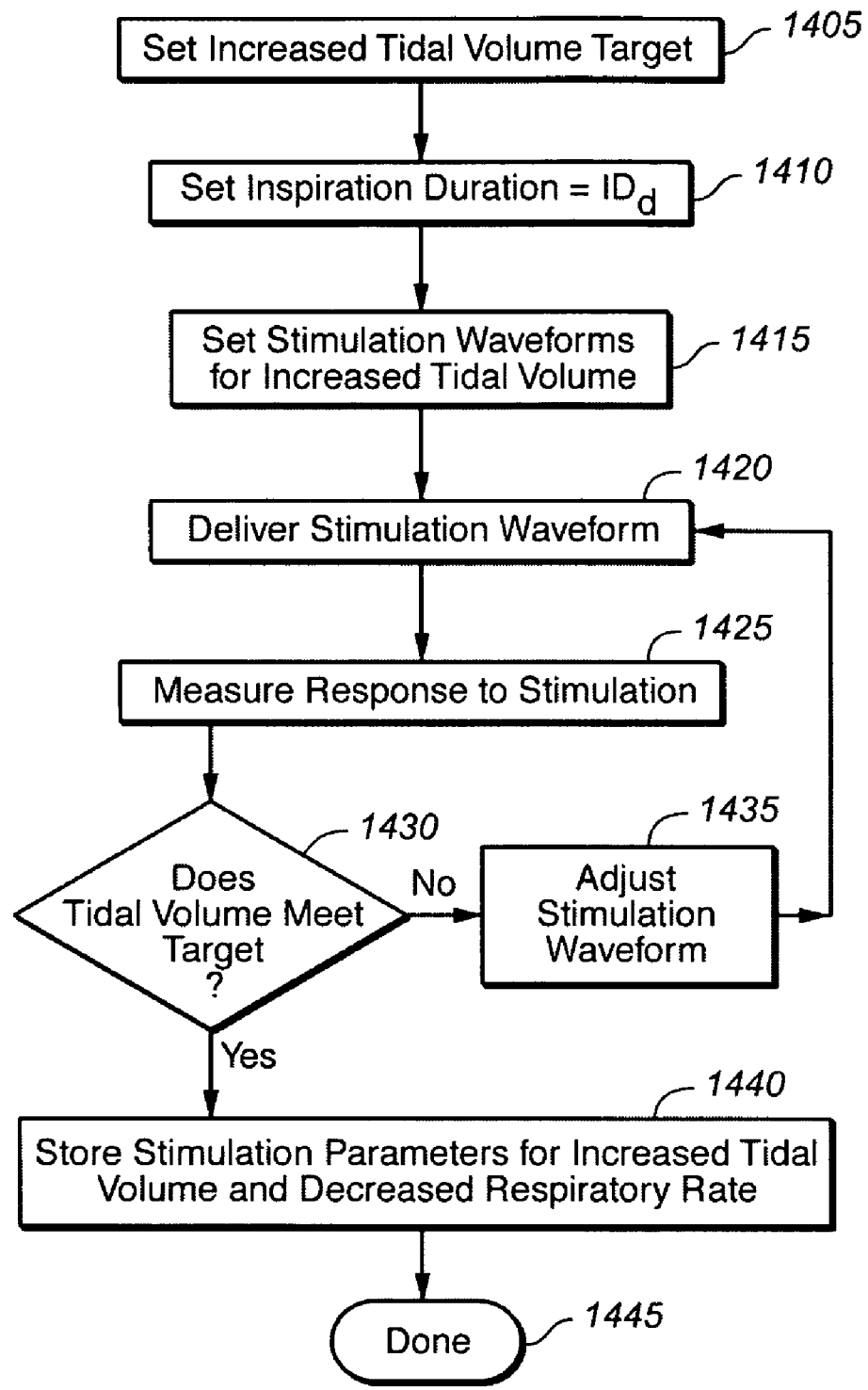
FIG. 14 shows a flow diagram for establishing stimulation waveforms with an increased tidal volume and a decreased respiratory rate in accordance with the invention.

FIG. 14 shows a flow diagram for establishing stimulation waveforms with an increased tidal volume and a decreased respiratory rate in accordance with a method embodiment of the present invention. In step 1405 the selected increased tidal value is selected as a target. In step 1410 the waveform inspiration duration is set to the $ID_d$ associated with the decreased respiratory rate.

In step 1415 the stimulation waveforms are given initial amplitude and frequency values, and initial amplitude and frequency ramp values. These values are selected to produce the selected increased tidal volume. The values may be selected on the basis of information specific to the subject such as previously observed mapping data.

In step 1420 the stimulation waveform is delivered to the diaphragm. In step 1425 the response to the stimulation waveform is measured. In step 1430 a criterion for accepting the response is evaluated. For example, the measured response tidal volume must be within a fixed percentage (e.g., 5%) of the target tidal volume of step 1405. If the criterion is not met step 1435 is executed. In step 1435 the stimulation waveform is adjusted. If the criterion is met in step 1430, step 1440 is executed. In step 1440 the waveform parameters are stored for increased tidal volume at decreased respiratory rate. In step 1445 the stimulation waveform parameters are established.

Figure 15:
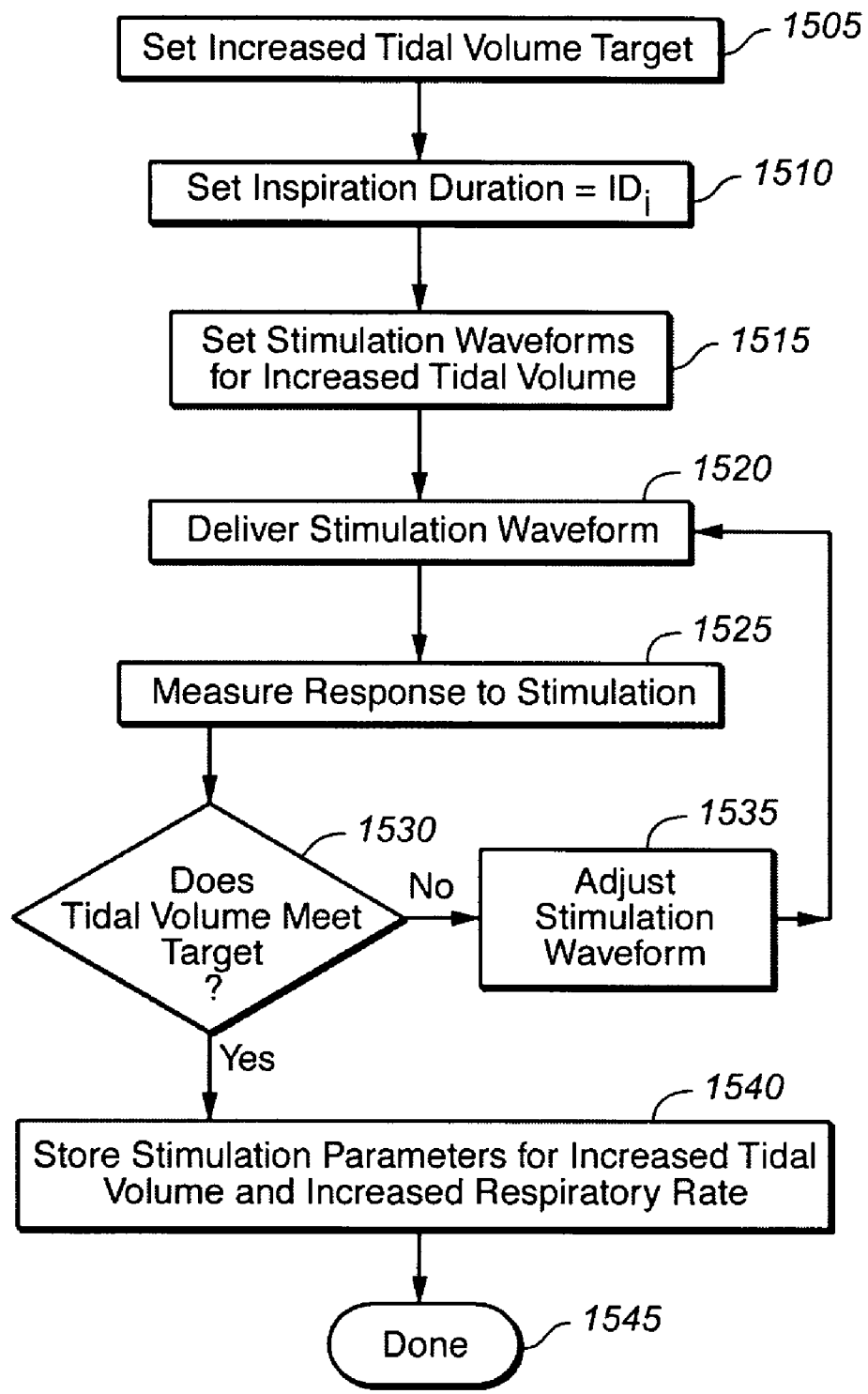
FIG. 15 shows a flow diagram for establishing stimulation waveforms with an increased tidal volume and an increased respiratory rate in accordance with the invention.

FIG. 15 shows a flow diagram for establishing stimulation waveforms with an increased tidal volume and an increased respiratory rate in accordance with a method embodiment of the present invention. In step 1505 the selected increased tidal value is selected as a target. In step 1510 the waveform inspiration duration is set to the $ID_i$ associated with the increased respiratory rate.

In step 1515 the stimulation waveforms are given initial amplitude and frequency values, and initial amplitude and frequency ramp values. These values are selected to produce the selected increased tidal volume. The values may be selected on the basis of information specific to the subject such as previously observed mapping data.

In step 1520 the stimulation waveform is delivered to the diaphragm. In step 1525 the response to the stimulation waveform is measured. In step 1530 a criterion for accepting the response is evaluated. For example, the measured response tidal volume must be within a fixed percentage (e.g., 5%) of the target tidal volume of step 1505. If the criterion is not met step 1535 is executed. In step 1535 the stimulation waveform is adjusted. If the criterion is met in step 1530, step 1540 is executed. In step 1540 the waveform parameters are stored for increased tidal volume at increased respiratory rate. In step 1545 the stimulation waveform parameters are established.

In use the system 100 is programmed to achieve increases and decreases in minute ventilation or other related parameters. The system 100 is then used to manipulate $PCO_2$ or $SaO_2$ levels by controlling minute ventilation or related respiration parameters that affect minute ventilation. Blood gas levels may be manipulated to prevent breathing disorders by stimulating the diaphragm after detecting a precursor to a breathing disorder. Examples of such detection and stimulation schemes are set forth in U.S. patent application entitled "Breathing Disorder and Precursor Predictor and Therapy Delivery Device and Method", Tehrani, et al., and incorporated herein by reference. The stimulation waveforms may also be used to control oxygen saturation levels to treat-heart failure patients, for example, periodically increasing oxygen saturation levels may be therapeutic to heart failure patients by either reducing the load on the heart and/or by having the patient breath in a more advantageous manner. Examples of such breathing therapies and therapy devices are described in U.S. patent application entitled "Breathing Therapy Device and Method", Tehrani, filed on even date herewith and incorporated in its entirety herein by reference.

A number of different parameters may be programmed into the processor to determine if certain breathing disorders are present, and when and how to stimulate respiration, and when to stop or modify stimulation.

Phrenic nerve or EMG activity sensed may include, for example, amplitude, frequency, and waveform to determine central respiratory efforts, the absence, a decrease in amplitude, abnormalities in frequency and/or amplitude, or waveform morphology of which may indicate the onset of apnea, hyperventilation, or hypoventilation. The nerve activity may be compared to predetermined activity levels or patient historical activity. Similarly, diaphragm EMG amplitude, frequency, waveform morphology and history may be used to determine apnea, hyperventilation and hypoventilation. For example, the nerve activity at the onset of sleep or after a given time in a reclining position, may be used as a baseline for comparison.

An awake sinus zone may be defined as a respiratory rate or range of rates programmed into the device for a specific patient when awake, where the respiratory rate is considered normal and intrinsic. A preprogrammed EMG amplitude or range may define a normal range in this state. A sleep sinus may be defined as a respiratory rate or range of rates programmed into the device for a specific patient when asleep where the respiratory rate is considered normal and intrinsic. A preprogrammed EMG amplitude or range may define a normal range in this state. The device may be programmed to match the EMG rate and amplitude to a normal rate and amplitude by auto adjusting the pace output.

Hypoventilation may be detected where the respiratory rate or frequency falls below a programmed rate. Hyperventilation may be detected when the respiratory rate or frequency is above a programmed rate. Complete apnea or central apnea is defined as a condition where there is no effective EMG signal or phrenic nerve signal, i.e. where there is no effective or significant physiological response. Frequently, a hyperventilation episode is followed by loss of diaphragm EMG or phrenic nerve activity. The device may be programmed to first detect the hyperventilation and wait for a preprogrammed time to be considered apnea. For example the time may be set to 10-20 seconds of lost EMG after a hyperventilation episode to detect complete apnea. Partial apnea or obstructive sleep apnea is defined to be present when the EMG or phrenic nerve activity is attenuated and may be detected when the amplitude drops below a programmed amount. For example such amount may be based on the EMG or phrenic nerve amplitude dropping a percentage, e.g. 50% of the Sleep Sinus EMG amplitude. Also the phase of the respiratory cycles in partial apnea may be determined or compared to an in phase cycle. An out of phase or arrhythmic cycle may also be used to detect partial apnea.

In addition, position sensors may be used to determine degree of patient reclining or standing, e.g., in increments of degrees. Information from the position sensor may be used as a tool to match respiratory activities and patterns to the position of the patient. Accelerometer information may be used to determine information regarding patient's physical activity, e.g., to match/compare to the respiratory patterns and activities and collect data on related patient activities, respiratory activities, and create or adjust a treatment plan based thereon, (e.g., modification of diuretics or ACE inhibitors). Accelerometer sensors may also be used to determine information regarding movement pattern of the diaphragm muscles, intercostal muscles, and rib movement and thus determine overall respiratory activity and patterns.

According to an embodiment, a stimulator includes an implantable controller coupled through leads to electrodes to be implanted on the diaphragm in the vicinity of the phrenic nerve branches. The electrodes may sense either nerve activity or EMG signals of the diaphragm. The stimulator may further include a pulse generator configured to deliver stimulating pulses, either to the same electrodes used for sensing or to additional stimulation electrodes. The stimulation electrodes may also be placed adjacent the phrenic nerve at some point along its length to provide stimulation pulse to the nerves, which in turn enervate the diaphragm muscle causing contractions and resulting respiration. Alternatively, the electrodes may be placed on the phrenic nerve for both sensing and stimulation.

Stimulation of respiration may be initiated when "no" or "attenuated" respiratory activity has been present or detected for a time period (when apnea is detected). The time period may be pre-programmed for a specific patient by the physician, as otherwise preset, or as determined a program in the treatment device. The device may be programmable for other breathing disorders, allowing slow or fast inspiration and visa versa allowing slow or fast expiration. For example, based on programmed parameters of the activity sensor, for patients suffering from hypoventilation, the inspiration rate may be increased or decreased based on the level of activity.

Figure 17:
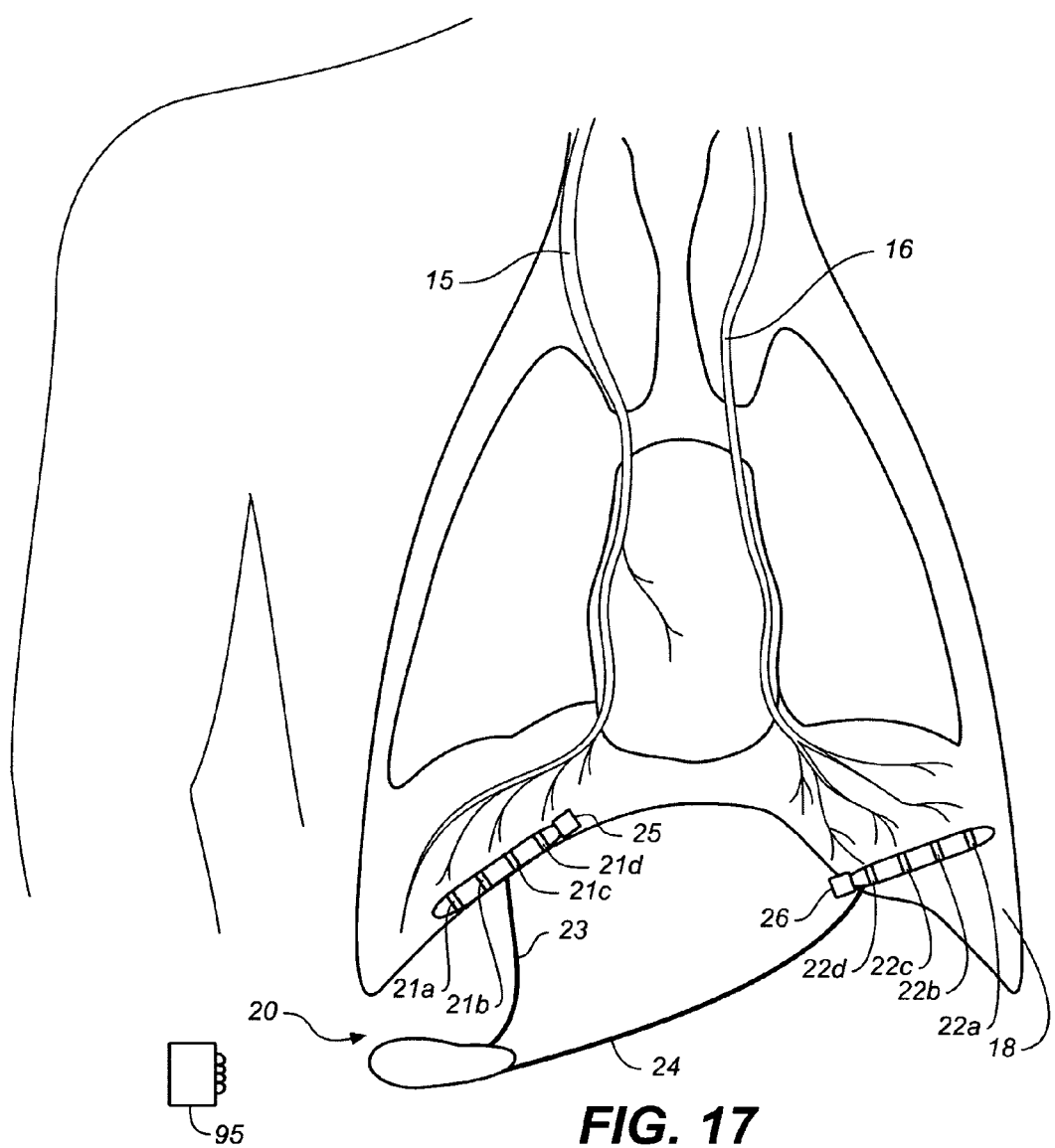
FIG. 17 illustrates a sleep breathing disorder treatment device in accordance with the invention placed on the diaphragm.

FIG. 17 illustrates a stimulator 20 comprising electrode assemblies 21, 22, each comprising a plurality of electrodes 21a-d and 22a-d respectively. The electrode assemblies 21, 22 are implanted in the diaphragm muscle so that one or more of electrodes 21a-d and of electrodes 22a-d are approximately adjacent to one or more junctions of the phrenic nerves 15, 16, respectively, with the diaphragm 18 muscle. The electrode assemblies 21, 22 sense and pace at the diaphragm muscle. They are implanted laparoscopically through the abdomen and into the muscle of the diaphragm 18 with needles or other similar devices. The electrode assemblies 21, 22 may be anchored with sutures, staples, or other anchoring mechanisms typically used with implantable EMG electrodes. The leads 23, 24 coupling the electrode assemblies 21, 22 to the control unit 90 are then routed subcutaneously to the side of the abdomen where a subcutaneous pocket is created for the control unit 90. The electrode assemblies 21, 22 are each flexible members (such as neurostimulation leads) with electrodes 21a-d, assembled about 5-20 mm apart from one another and electrodes 22a-d assembled about 5-20 mm apart from one another. The electrode assemblies 21, 22 are coupled via leads 23, 24 to control unit 90. The control unit 90 is configured to receive and process signals corresponding to sensed nerve activity, and/or EMG of the diaphragm 18, to determine the respiratory parameters of the diaphragm 18 as described in more detail herein with reference to FIGS. 22, 23A-23B and 24A-24D.

The electrodes assemblies 21, 22 are coupled via leads 23, 24 to input/output terminals 101, 102 of a control unit 90. The leads 23, 24 comprise a plurality of electrical connectors and corresponding lead wires, each coupled individually to one of the electrodes 21a-d, 22a-d. The control unit 90 is implanted subcutaneously within the patient, for example in the chest region on top of the pectoral muscle. The control unit 90 is configured to receive sensed nerve electrical activity from the electrode assemblies 21, 22, corresponding to respiratory effort of a patient. The control unit 90 includes a processor 105 (FIG. 22) that delivers stimulation to the nerves 15,16 or diaphragm 18 in response to a sensed degree or absence of diaphragm respiratory effort as determined and processed by the processor 105 and control unit 90 as described in more detail herein with reference to FIGS. 22, 23A-23B, and 24A-24D.

The stimulator 20 also comprises movement detectors 25, 26, in this example, strain gauges included with the electrode assemblies 21, 22 respectively and electrically connected through leads 23, 24 to the control unit 90. The movement detectors 25, 26 detect movement of the diaphragm 18 and thus the respiratory effort exerted by the diaphragm 18. The movement detectors 25, 26 sense mechanical movement and deliver a corresponding electrical signal to the control unit 90 where the information is processed by the processor 105. The movement may be used to qualify the electrical phrenic nerve or EMG signal sensed by the device to confirm inspiration or exhalation is occurring, e.g., by matching mechanical and electrical activities of the diaphragm.

Electrodes may be selected from the plurality of electrodes 21a-d and 22a-d (or electrodes 41a-h, 42a-h, 61a-d, 62a-d, 71a-d, 72a-d in the other examples described herein) once implanted, to form bipolar or multipolar electrode pairs or groups that optimize the stimulation response. Such desired response may include tidal volume, breathing rate and the slopes of the inhalation and exhalation curves. For example, a timed series of pulses may be used to create a desired respiratory inhalation and/or exhalation period. Testing the response may be done by selecting a bipolar electrode pair from two of the multiple electrodes in an assembly or any other combination of electrodes to form at least one closed loop system, by selecting sequence of firing of electrode groups and by selecting stimulation parameters. The electrodes may be selected by an algorithm programmed into the processor that determines the best location and sequence for stimulation and/or sensing nerve and/or EMG signals, e.g., by testing the response of the electrodes by sensing respiratory effort in response to stimulation pulses. Alternatively, the selection process may occur using an external programmer that telemetrically communicates with the processor and instructs the processor to cause stimulation pulses to be delivered and the responses to be measured. From the measured responses, the external programmer may determine the optimal electrode configuration, by selecting the electrodes to have an optimal response to a bipolar or multipolar delivery of stimulation.

Figure 18:
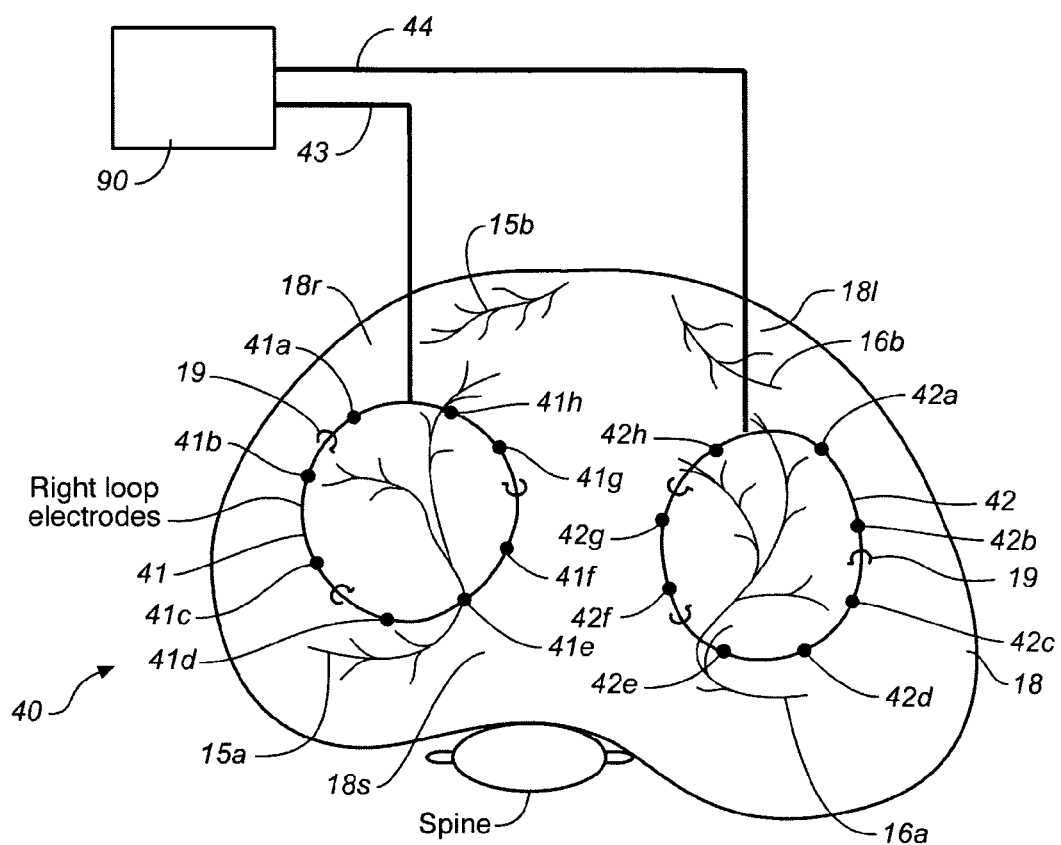
FIG. 18 illustrates an electrode assembly in accordance with the invention implanted on the abdominal side of the diaphragm.

FIG. 18 illustrates a diaphragm electrode assembly 40 in accordance with the invention for placement on the diaphragm 18 for sensing and/or stimulation of the diaphragm and/or phrenic nerve endings located in the diaphragm 18. The assembly 40 comprises a right loop 41 and a left loop 42, each loop comprising a plurality of electrodes 41a-h and 42a-h, each having individual connectors and leads that form leads 43, 44 coupled to the control unit 90. The loops 41, 42 are similar to electrode assembles 41, 42 in that the electrodes are selectable by the control unit 90 to form electrode pairs, multiple electrode pairs, or multipolar electrode groups. FIG. 2 illustrates right phrenic nerve endings 15a and left phrenic nerve endings 16a as well as the right phrenic nerve anterior branch 15b, and left phrenic nerve anterior branch 16b, located on the diaphragm abdominal surface 18s. The loops 41, 42 are flexible and are placed on the abdominal surface 18s of the diaphragm 18 on the right diaphragm 18r and left diaphragm 18l, respectively adjacent the right phrenic nerve endings 15a and left phrenic nerve endings 16a respectively. The flexibility of the loops 41, 42 permits the ability to form the loops is the shape most ideally suite for a particular patient. The loops 41, 42 are attached to the diaphragm 18 with sutures, staples or other attachment devices 19. Other shapes may be used as well, e.g. a loop with a branch that extends to the region adjacent the anterior branches 15b, 16b of the phrenic nerve. The control unit 90 may be programmed to activate the electrodes in a sequence that is determined to elicit the desired response from the diaphragm 18 as described above with reference to electrodes 21a-d, 22a-d and FIG. 1.

Figure 19:
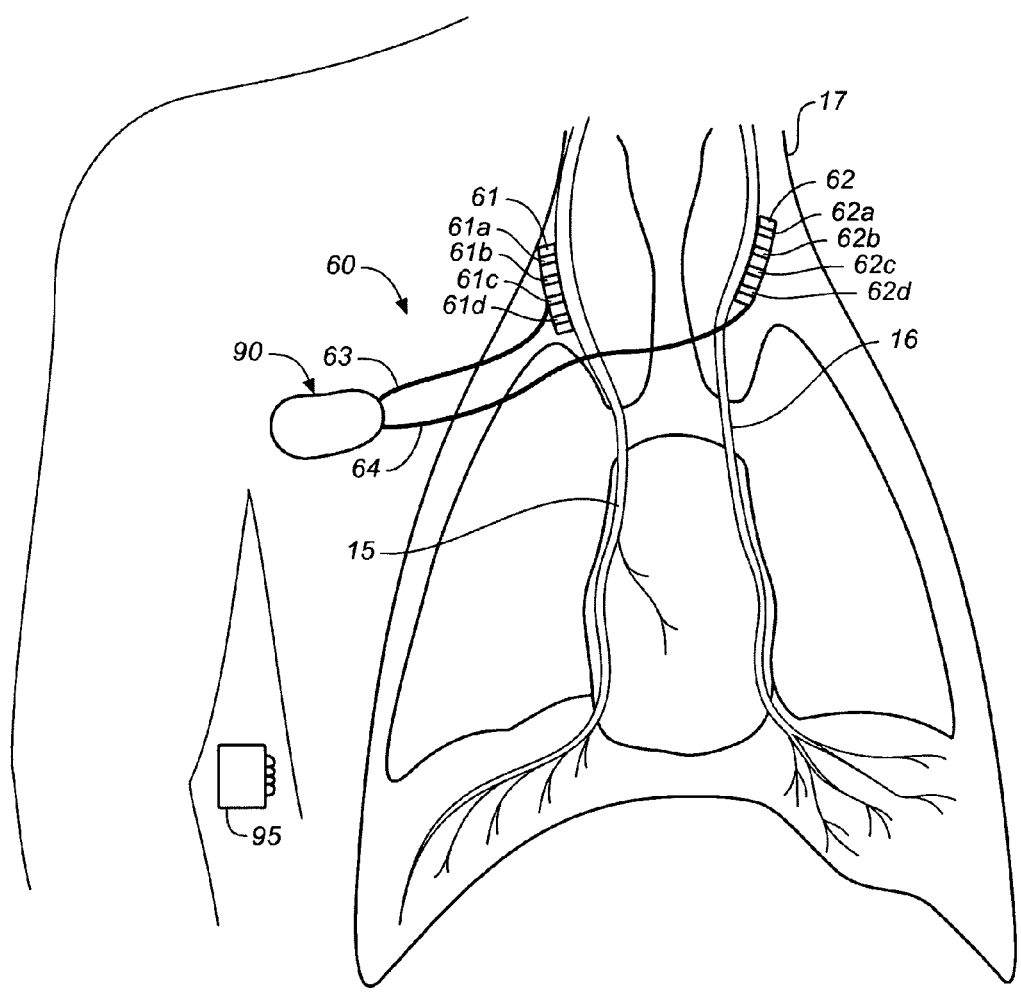
FIG. 19 illustrates a sleep breathing disorder treatment device in accordance with the invention placed on the phrenic nerves.

Referring to FIG. 19, a breathing disorder treatment apparatus 60 according to the invention is illustrated. The apparatus 60 comprises right and left electrode assemblies 61, 62 each comprising a plurality of electrodes 61a-61d and 62a-62d respectively. The electrodes assemblies 61, 62 are illustrated attached to the right and left phrenic nerves 15, 16, respectively at a location in the neck 17. The electrode assembly may be a curved cuff electrode that can be placed around the nerve. Procedures for accessing and attaching such electrode assemblies are generally know, for example, as described in Phrenic Nerve Stimulation For Diaphragm Pacing With a Spinal Cord Stimulator, Sur. Neurol 2003:59: 128-32.

Figure 20:
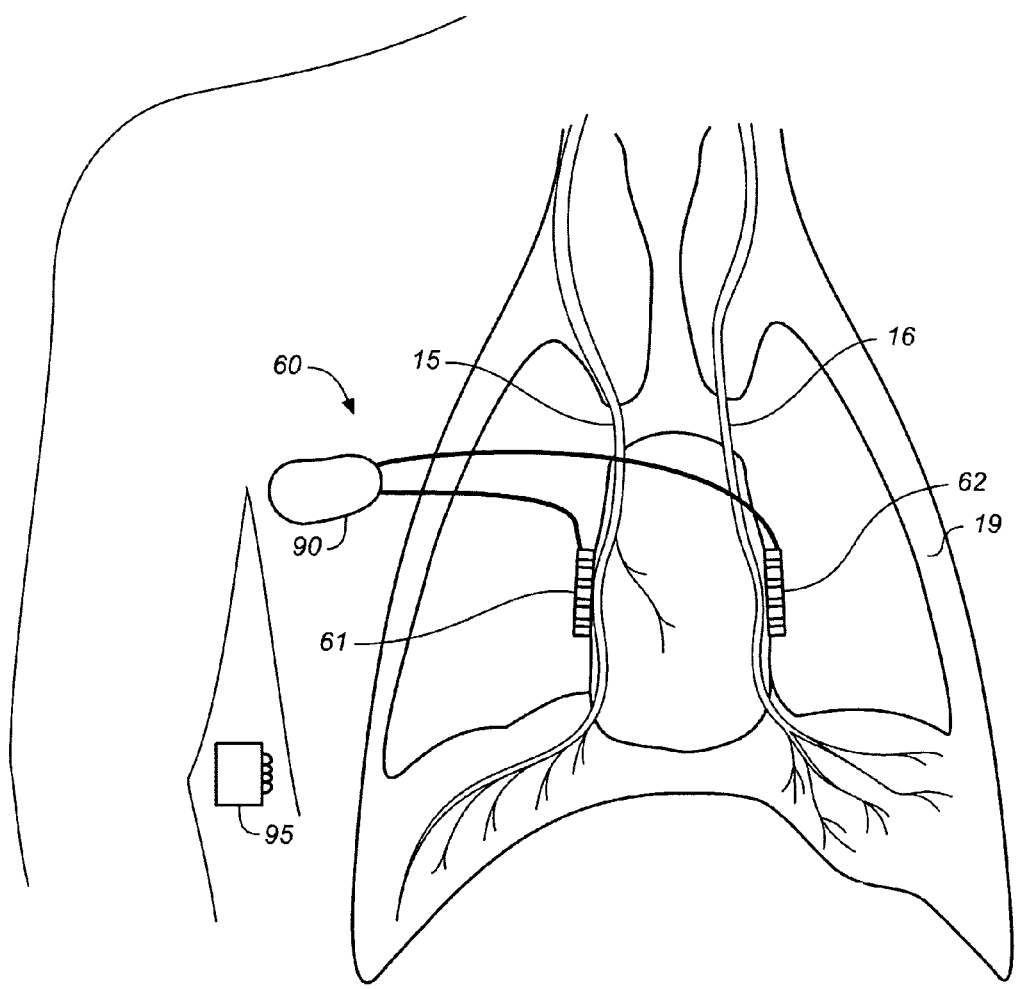
FIG. 20 illustrates a sleep breathing disorder treatment device in accordance with the invention placed on the diaphragm and phrenic nerves.

FIG. 20 illustrates the device 60 of to FIG. 19 with electrode assemblies 61, 62 alternatively positioned within the thorax 19 on the phrenic nerves 15, 16. The electrode assemblies 61, 62 are placed thoracoscopically on the phrenic nerve using a procedure similar to that described in Thoracoscopic Placement of Phrenic Nerve Electrodes for Diaphragmatic Pacing in Children; Journal of Pediatric Surgery, Vol. 37, No 7 (July), 2002: pp 974-978. The electrode assemblies 61, 62 are located between the third and fourth rib within the thorax 19. The stimulator 60 is used in a similar manner in this FIG. 20 as it is with reference to FIG. 19.

Figure 21:
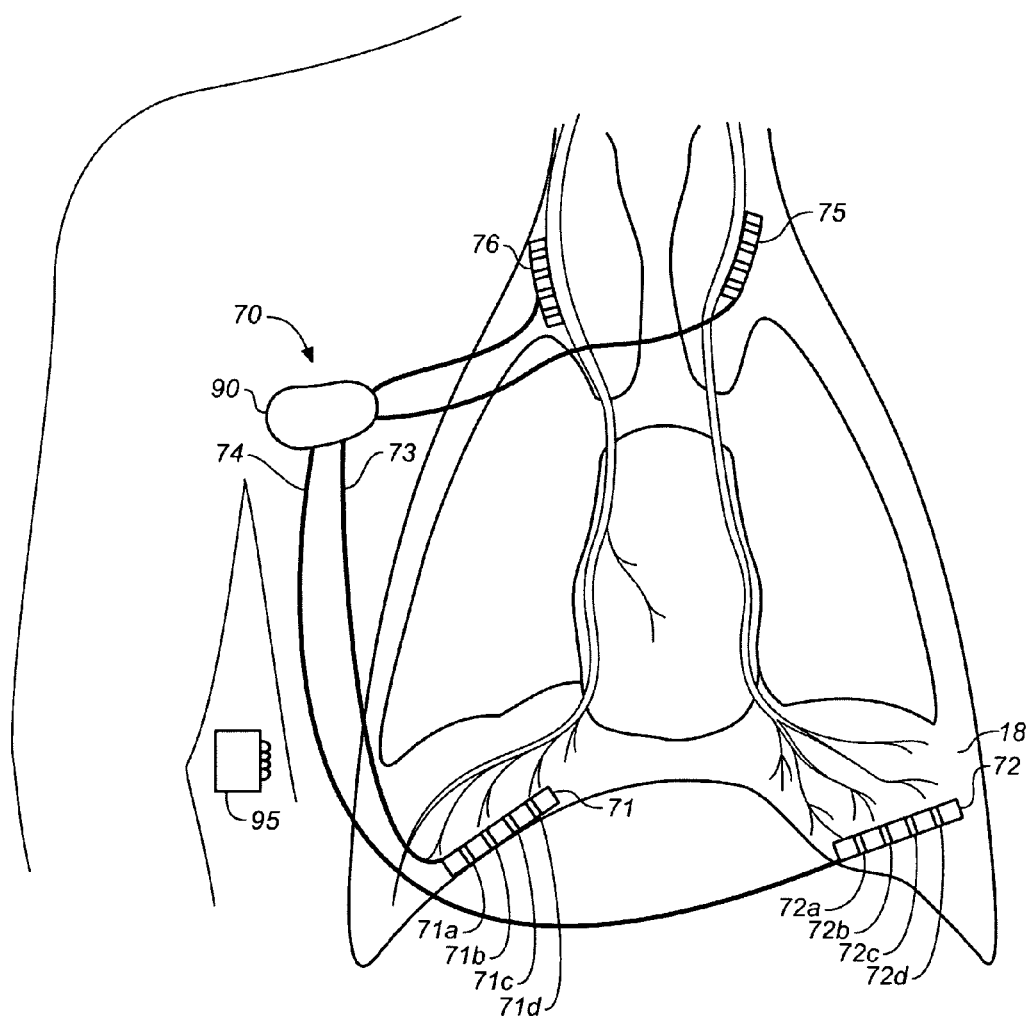
FIG. 21 illustrates a sleep breathing disorder treatment device in accordance with the invention placed on the phrenic nerves.

FIG. 21 illustrates a stimulator 70 in accordance with the invention. The stimulator comprises stimulating electrode assemblies 71, 72 implanted in the diaphragm in a manner similar to that described above with reference to electrode assemblies 71, 72 in FIG. 17. The electrode assemblies 71, 72 include electrodes 71 a-d, 72a-d, configured to deliver stimulating pulses to the diaphragm and or phrenic nerve branches or junctions with the diaphragm to elicit a breathing response by causing the diaphragm to move. The stimulator 70 further comprises electrode sensor assemblies 75, 76 placed on the phrenic nerve at the throat in a surgical procedure similar to that described above with reference to FIG. 17 and electrode assemblies 71, 72. The sensor assemblies 75, 76 comprise a plurality of electrodes that are positioned and configured to sense electrical activity of the phrenic nerve to determine central respiratory effort. In response to sensed respiratory effort, the control unit 90 supplies EMG and/or nerve stimulation to the muscles of the diaphragm 18 and/or the phrenic nerve endings 15, 16 located in the diaphragm 18.

Figure 22:
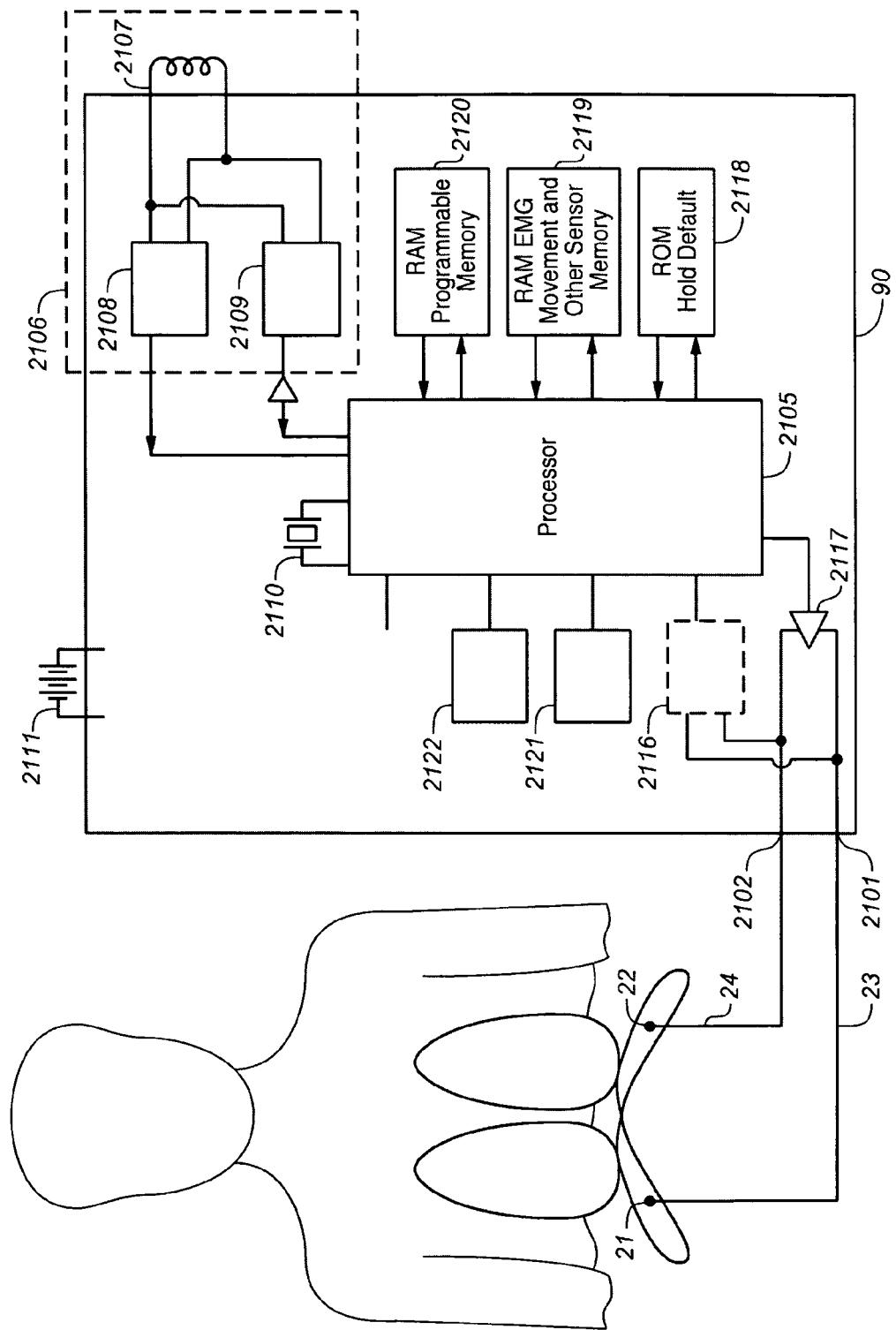
FIG. 22 illustrates a processor unit of a sleep breathing disorder treatment device in accordance with the invention.

FIG. 22 illustrates an implantable control unit 90. The control unit 90 includes electronic circuitry capable of generating and/or delivering electrical stimulation pulses to the electrodes of electrode assemblies 21, 22, 41, 42, 61, 62, 71, 72 through leads 23, 24, 43, 44, 63, 64, 73, 74 respectively to cause a diaphragm respiratory response in the patient. For purposes of illustration, in FIG. 6, the control unit 90 is illustrated coupled to through leads 23, 24 to electrode assemblies 21, 22 respectively. Other leads 41, 42, 61, 62, 71, 72 as described herein may be connected to inputs 2101, 2102.

The control unit 90 comprises a processor 2105 for controlling the operations of the control unit 90. The processor 2105 and other electrical components of the control unit are coordinated by an internal clock 2110 and a power source 2111 such as, for example a battery source or an inductive coupling component configured to receive power from an inductively coupled external power source. The processor 2105 is coupled to a telemetry circuit 2106 that includes a telemetry coil 2107, a receiver circuit 2108 for receiving and processing a telemetry signal that is converted to a digital signal and communicated to the processor 2105, and a transmitter circuit 2109 for processing and delivering a signal from the processor 2105 to the telemetry coil 2107. The telemetry coil 2107 is an RF coil or alternatively may be a magnetic coil. The telemetry circuit 2106 is configured to receive externally transmitted signals, e.g., containing programming or other instructions or information, programmed stimulation rates and pulse widths, electrode configurations, and other device performance details. The telemetry circuit is also configured to transmit telemetry signals that may contain, e.g., modulated sensed and/or accumulated data such as sensed EMG activity, sensed nerve activity, sensed responses to stimulation, sensed position information, sensed movement information and episode counts or recordings The leads 23, 24 are coupled to inputs 2101, 2102 respectively, of the control unit 90, with each lead 23, 24 comprising a plurality of electrical conductors each corresponding to one of the electrodes or sensors (e.g., strain gauge) of the electrode assemblies 23, 24. Thus the inputs 2101, 2102 comprise a plurality of inputs, each input corresponding to one of the electrodes or sensors. The signals sensed by the electrode assemblies 21, 22 are input into the control unit 90 through the inputs 2101, 2102. Each of the inputs are coupled to a separate input of a signal processing circuit 2116 (schematically illustrated in FIG. 22 as one input) where the signals are then amplified, filtered, and further processed, and where processed data is converted into a digital signal and input into the processor 2105. Each signal from each input is separately processed in the signal processing circuit 2116.

The EMG/Phrenic nerve sensing has a dual channel sensor. One corresponding to each lung/diaphragm side. However, sensing can be accomplished using a single channel as the brain sends signals to the right and left diaphragm simultaneously. Alternatively, the EMG or phrenic nerve collective may be sensed using a single channel. Either a dual channel or single channel setting may be used and programmed. The typical pulse width parameter will range from 0.5 ms to 10 ms in increments of 50 µs. The pulse amplitude is from about 0.1 v to 5 volts in increments of 100 µV. The refractory period is 1 to 10 seconds in increments of 1 second. As described in more detail with reference to FIGS. 25A-25B herein the system may adjust the pace, pulse, frequency and amplitude to induce or control rate of the various portions of a respiratory cycle, e.g. slope of inspiration, fast exhalation, exhalation and tidal volume. The system may also adjust the rate of the respiratory cycle.

The system EMG memory is programmable to pre-trigger and post trigger lengths of storage for sleep apnea episodes. The pre-trigger events are the waveform signals and other sensed information observed transitioning to an event. Post-trigger events are the waveforms and other sensed information observed after an event and/or after treatment of an event, to observe how the device operated. Post-trigger recordings can confirm if the episode was successfully treated. The pre-trigger and post-trigger time periods can be preprogrammed into the control unit 90.

The control unit 90 includes a position sensor 121 configured to sense a relative position of the patient, e.g. angular position, and provide a digital signal corresponding to the sensed position to the processor 105.

The control unit 90 also includes an accelerometer 2122 configured to sense acceleration and movement of the patient and to provide a digital signal corresponding to the sensed movement to the processor 105. In addition, an accelerometer 122 is positioned within the control unit 90. The accelerometer 122 measures the activity levels of the patient and provides the signal to the processor 2105 for use in further analysis. Using an accelerometer in the implanted device indicates the activity level of the patient in conjunction with breathing rate. The accelerometer senses activity threshold as at rest, low medium or high depending on the programmed threshold value for a specific patient. Using the activity (accelerometer) sensor value and respiratory information, the health of the respiratory system may be evaluated and monitored. For example, if a patient's respiratory rate increases with an increase in activity and decreases with a decrease in activity, within a normal range, the patient's system will be considered functioning normally. If the patient's respiratory rate is out of range or too high while the activity sensor indicates at rest or low, then the patient may be suffering from pulmonary edema. Using this monitor, the effect of drug titrations, e.g., diuretic dosages, on a patient with pulmonary edema can be monitored. If the pulmonary edema patient's respiration is brought more towards a normal range with a drug dose, then the drug treatment would be maintained. lithe drug treatment did not effect breathing sufficiently then the drug dosage may be increased. Accordingly, the drug dosage may vary with detected breathing irregularities.

A position sensor 2121 is also located within the control unit 90 and has an output coupled to the processor 105. The position sensor senses the relative angle of the patients' position. The position sensor is used to detect a patient's relative position, e.g., horizontal, supine, or standing. An available position sensor is the Spectrol 601-1045 smart position sensor, self-contained device that provides an analog output over a full range of 360 degrees without requiring external components.

The control unit 90 further includes a ROM memory 2118 coupled to the processor 2105 by way of a data bus. The ROM memory 2118 provides program instructions to the control unit 90 that direct the operation of the stimulator 40. The control unit 90 further comprises a first RAM memory 2119 coupled via a data bus to the processor 2105. The first RAM memory 2119 may be programmed to provide certain stimulation parameters such as pulse or burst morphology; frequency, pulse width, pulse amplitude, duration and a threshold or trigger to determine when to stimulate. A second RAM memory 2120 (event memory) is provided to store sensed data sensed, e.g., by the electrodes 21*a-d* 22*a-d*, 41*a-h* 42*a-h*, 61*a-d* 62*a-d*, 71*a-d*, 72*a-d* (EMG or nerve activity), position sensor 2121, diaphragm movement sensors or strain gauges 25, 26, or the accelerometer 2122. These signals may be processed and used by the control unit 90 as programmed to determine if and when to stimulate or provide other feedback to the patient or clinician. Also stored in RAM memory 2120 may be the sensed waveforms for a given interval, and a count of the number of events or episodes over a given time as counted by the processor 2105. The system's memory will be programmable to store: number of sleep apnea episodes per night; pacing stimulation and length of time; the systemic auto-correction (i.e., how stimulus was adjusted, e.g., in amplitude frequency phase or waveform, to reach a desired or intrinsic level response); body resumption of breathing; the number of apnea episodes with specific durations and averages and trending information; hyperventilation episodes during supine position; number of hyperventilation episodes during sleep position; number of hyperventilation episodes during vertical position; and patient information including the medications and dosages and dates of changes. These signals and information may also be compiled in the memory and downloaded telemetrically to an external device 95 when prompted by the external device 95.

An example of the circuits of the signal processing circuit 2116 corresponding to one of the EMG inputs for one of the electrodes or pairs of electrodes of the assemblies 21, 22 is illustrated schematically in FIG. 7A. An EMG signal is input into an amplifier 2130 that amplifies the signal. The signal is then filtered to remove noise by filter 2131. The amplified signal is rectified by a rectifier 2132, is converted by an A/D converter 2133 and then is integrated by integrator 2134 to result in an integrated signal from which respiratory information can be ascertained. The signal output of the integrator 2134 is then coupled to the processor 2105 and provides a digital signal corresponding to the integrated waveform to the processor 2105. The signal output of the integrator 2134 is also coupled to a peak detector 135 that determines when the inspiration period of a respiratory cycle has ended and an expiration cycle has begun. The signal output of the integrator 2134 is further coupled to a plurality of comparators 2136, 2137, 2138, 2139. The first comparator 2136 determines when respiration (EMG signal or phrenic nerve signal) has been detected based on when an integrated signal waveform amplitude has been detected that is greater than a percentage value of the peak of an intrinsic respiratory cycle or another predetermined amount (comp 1), for example between 1-25% of the intrinsic signal. In this example, the comparator is set at a value that is 10% of the waveform of an intrinsic respiratory cycle. The second comparator 2137 determines a value of the waveform amplitude (comp 2) when an integrated signal waveform amplitude has been detected that is at a predetermined percentage value of the peak of an intrinsic respiratory cycle or another predetermined amount, for example between 75%-100% of the intrinsic signal. In this example, the comparator is set at a value that is 90% of the waveform of an intrinsic respiratory cycle. From this value and the comp 1 value, the slope of the inspiration period (between 10% and 90% in this example) may be determined. This slope may provide valuable diagnostic information as it shows how quickly a patient inhales. After (or when) the peak detector detects the end of an inhalation period and the beginning of an exhalation period, the third comparator 2138 determines an upper value for the waveform amplitude during active exhalation period, for example between 100% and 75% of the peak value detected by the peak detector 2135. Then a lower value (comp 4) of the waveform during the exhalation period is determined by the fourth comparator 2139, which compares the measured amplitude to a predetermined value, e.g. a percentage value of the peak amplitude. In this example the value is selected to be 10% of the peak value. In one embodiment this value is selected to roughly coincide with the end of a fast exhalation period. From comp 3 and comp 4 values, the slope of the exhalation period (between 10% and 90% in this example) may be determined. This slope may provide valuable diagnostic information as it shows how quickly a patient exhales.

Figure 23A:
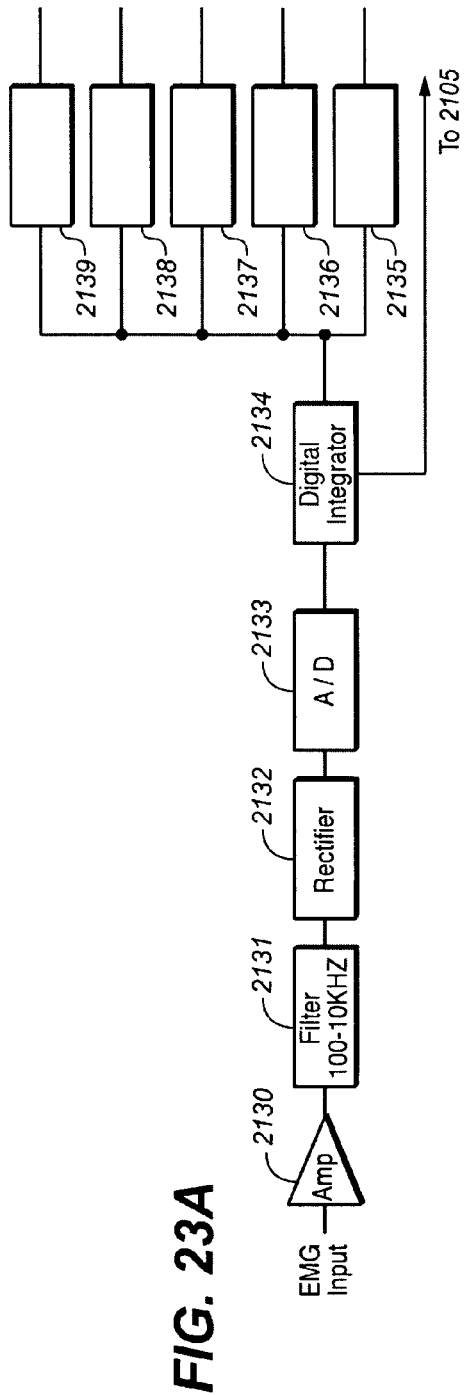
FIG. 23A is a schematic of a signal processor of the processor unit in accordance with the invention.
Figure 23B:
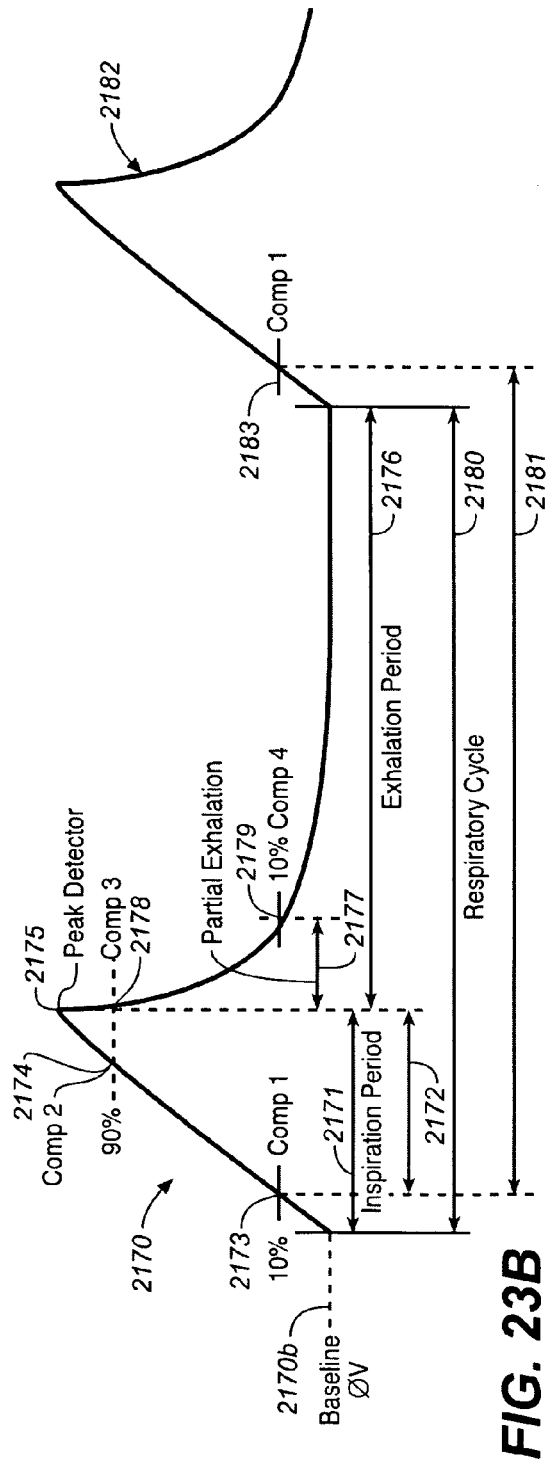
FIG. 23B is an example of a waveform of an integrated signal processed by the signal processor of FIG. 7A.

FIG. 23B illustrates two sequential integrated waveforms of exemplary integrated signals corresponding to two serial respiratory cycles, described in more detail herein with reference to FIGS. 24A-24D. The waveform 2170 has a baseline 2170*b*, inspiration cycle 2171, a measured inspiration cycle 2172, a point of 10% of peak inspiration 2173 (comp 1), a point of 90% of peak of inspiration 2174 (comp 2), a peak 175 where inspiration ends and exhalation begins, and exhalation cycle 2176 a fast exhalation portion 2177 of the exhalation cycle 2176, a 90% of peak exhalation point 2178 (comp 3), a 10% of peak exhalation point 2179 (comp 4), an actual respiratory cycle 2180 and a measured respiratory cycle 2181. The second waveform 2182 is similarly shaped. The 10% inspiration 2183 of the second waveform 182 marks the end of the measured respiratory cycle 181, while the 10% point 2173 of the waveform 2170 marks the beginning of the measured respiratory cycle 2181.

The system may adjust the pace, pulse, frequency and amplitude to induce slow and elongated inspiration period; and fast and short inspiration period. The system may match the intrinsic sleep or awake time tidal volume by adjusting the output energy while sensing the EMG or nerve amplitude. This may be done gradually by frequently sensing and incrementally adjusting. The system may deliver elongated inspiration period while shortening the expiration period to control and manipulate the $PO_2$ and $PCO_2$ levels in the blood to overcome and treat apnea. The system may deliver time and amplitude modulation output for control of inspiration and exhalation periods. To increase the inspiration period, the system may deliver fewer bursts at lower amplitudes and higher frequencies. To create a fast, short inspiration cycle, the system may deliver more of bursts at higher amplitudes. The system may deliver sequential low energy pacing output either from one or multiple electrodes to control and manage the pulmonary stretch receptor threshold levels to avoid or prevent the collapse of the upper airways. FIG. 25 illustrates a variety of exemplary stimulation bursts and resulting effective EMG that may be used to control the various phases of the respiratory cycle, including, e.g., slope of inspiration, fast exhalation, exhalation, tidal volume, peak value, and rate of respiration.

Referring to FIGS. 25A-25B, a first intrinsic EMG waveform 2550 is illustrated in FIG. 25A. A subsequent EMG waveform 2551 (FIG. 25A) is illustrated in response to a burst of pulses 2561 (FIG. 25B) of symmetric amplitude, frequency and pulse width. A subsequent EMG waveform 2552 is illustrated (FIG. 25A) in response to burst of pulses 2562 (FIG. 25B). The resulting EMG waveform 2552 (FIG. 25A) has a flatter inspiration slope and expiration slope and relatively lower peak amplitude. This particular effect may be desirable to control breathing and create a slower more gradual inspiration. The burst 2562 (FIG. 25B) comprises a series of pulses increasing in amplitude and of a higher frequency than burst 2561 (greater number of pulses). The subsequent EMG waveform 2553 (FIG. 25A) has a relatively sharp inspiration slope. The corresponding burst 2563 of pulses has fewer pulses (3) and higher amplitude pulses. The effect of this burst 2563 is to increase inspiration rate. The subsequent EMG waveform 2554 (FIG. 25A) has a relatively slow inspiration cycle as a result of a burst 2564 (FIG. 25B) with both increasing amplitudes and longer pulse widths (and a greater pulse duration). These are a few examples of a multitude of possible variations of burst pulses that can be modified to control the inspiration, expiration, tidal volume (area under waveform curve) and other parameters of the respiratory cycle by modifying frequency, amplitude, pulse width of the pulses within the burst and the duration of the burst to get a desired effect. These bursts can be modified and programmed into a stimulator and may vary from patient to patient.

An external device may be configured to transmit signals to the implanted control unit 90 containing, e.g., programming or other instructions or information, programmed stimulation rates and pulse widths, electrode configurations, and other device performance details.

Figure 24A:
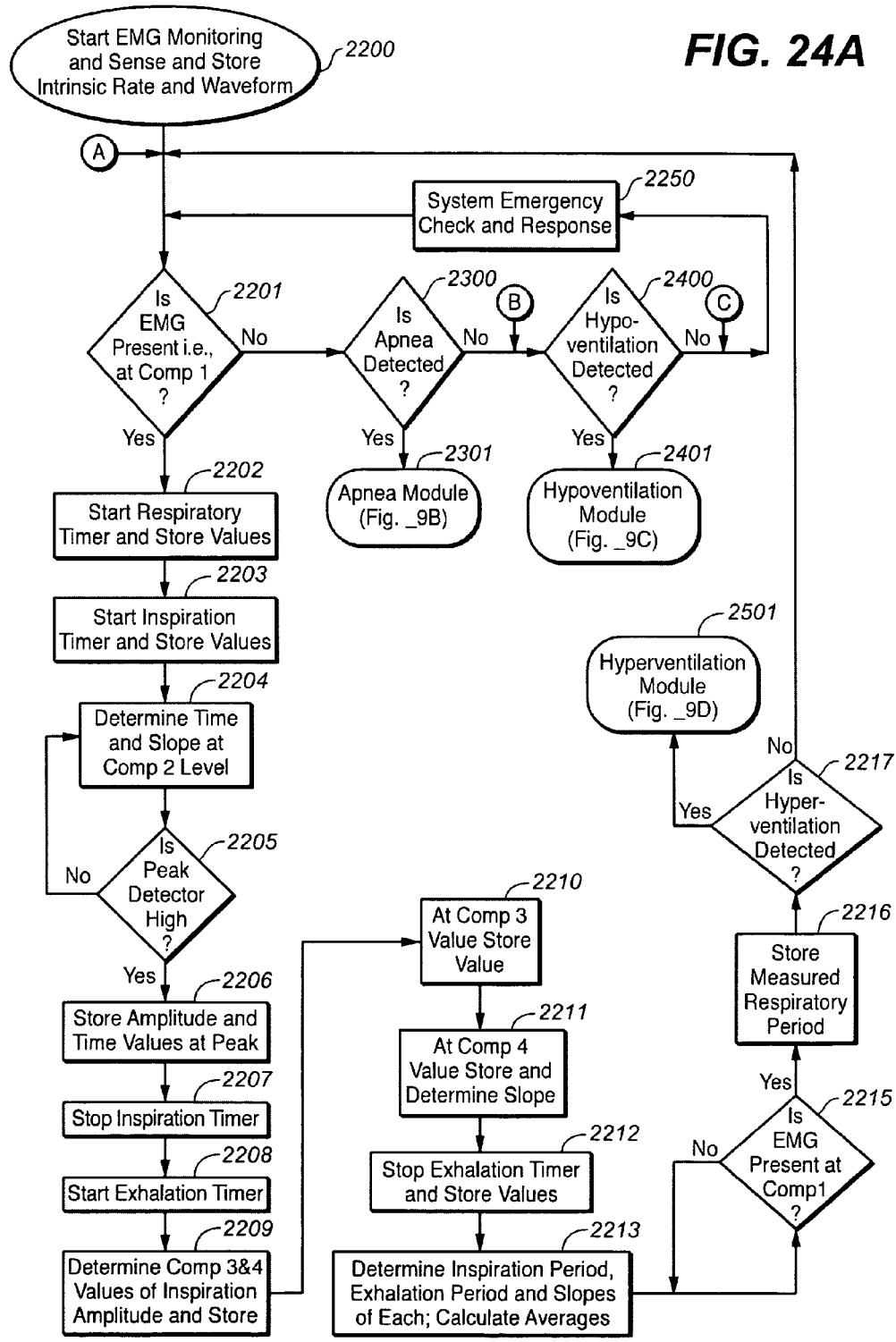
FIGS. 24A-24D are flow diagrams of the operation of a stimulator in accordance with the invention.
Figure 24B:
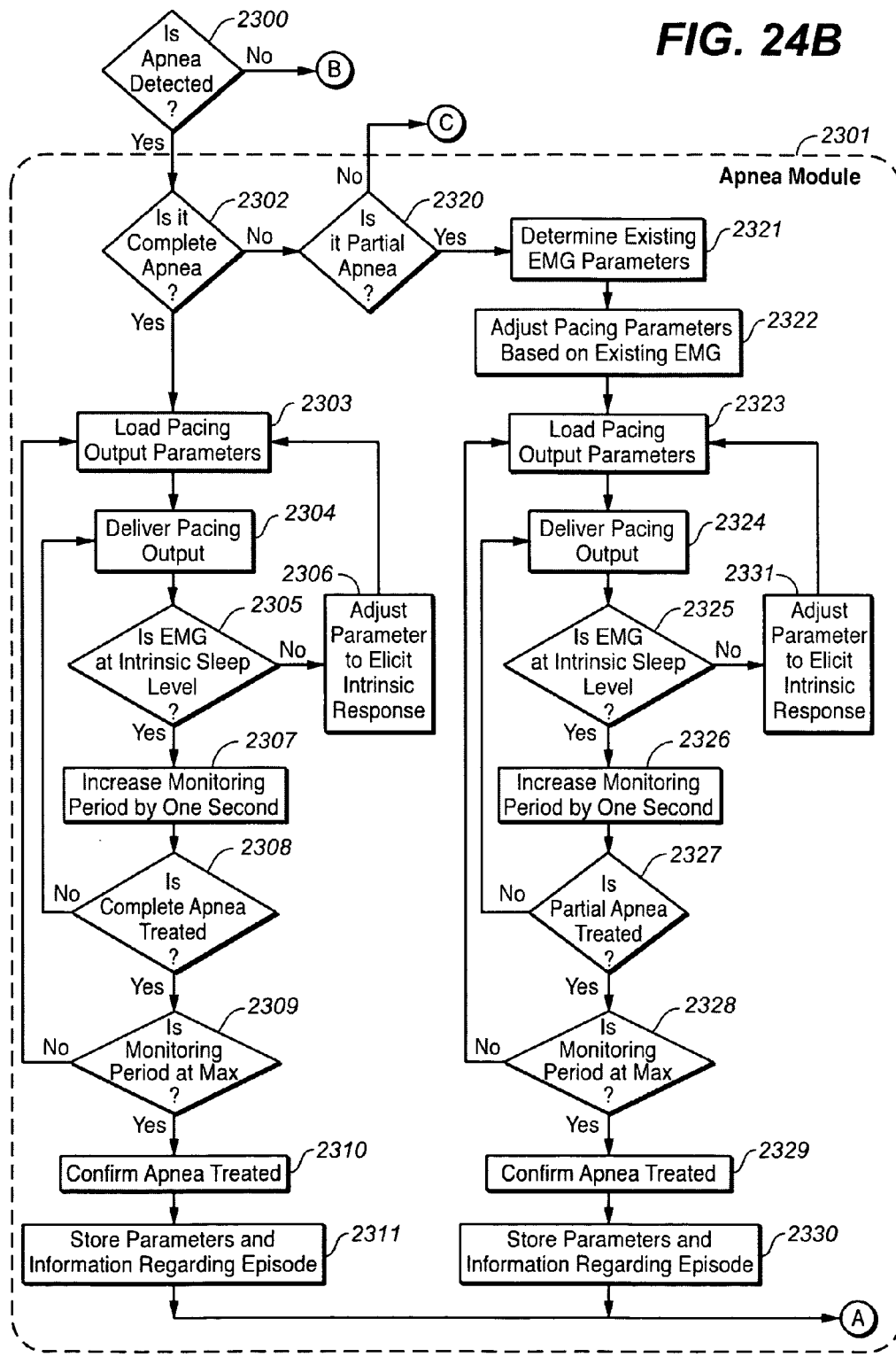

FIGS. 24A-24D illustrate the operation of a stimulator in accordance with the invention. The EMG monitoring is turned on or started 2200. (Alternatively, or additionally, the phrenic nerve activity may be monitored in the sequences described in FIGS. 24A-24D). As illustrated in FIG. 24A-24B, the system is turned on and begins sensing respiratory effort. It determines the intrinsic rates of breathing cycles including respiratory period, inhalation period and exhalation period, and stores the values in event memory (step 2200). This may be done, e.g., by sensing when a patient is in a reclining position for a predetermined period of time while their breathing normalizes to that near the breathing rate when sleeping. A threshold level is then calculated from the intrinsic rate at some level below the peak of the intrinsic respiratory effort level.

The presence of an EMG is detected 2200 by detecting when the amplitude of the integrated waveform 2170 reaches a predetermined level, e.g., at a percentage of the total amplitude, of the intrinsic waveform of the breathing rate when sleeping.

If there is no EMG detected 2201 then the stimulator determines whether sleep apnea is present or not 300 by determining a lack of EMG or phrenic nerve activity in a given period of time, e.g., 5-10 seconds, or by an attenuated EMG, e.g., not reaching comp 1 or, e.g., not reaching comp 2 in the case of partial apnea. If sleep apnea is present, then the stimulator goes to the apnea treatment module 2301 or to a program where the apnea is treated (See FIG. 24B). If sleep apnea is not detected, then the stimulator determines if hypoventilation is present 2400 by determining that the EMG is present at an intrinsic amplitude or percentage thereof, but the rate is lower than the intrinsic rate. If hypoventilation is present then the stimulator goes to the hypoventilation treatment module 2401 or to a program where hypoventilation is treated. (See FIG. 24C.) If an EMG, apnea, and hypoventilation are not detected, then presumably the patient is not breathing or there is a malfunctioning of the stimulator. If this is the case, the system may be programmed to do an emergency check of the components and then communicate to the patient or health care provider that the stimulator is malfunctioning and/or the patient is not breathing 250. This communication may be accomplished a number of ways via a variety of ongoing or periodic communication processes. The system may continue to listen for an EMG 2201 after the system does and emergency check (step 2250). After a given time or number of iterations of reaching step 2250, the stimulator may sound an alarm.

If an EMG is detected at step 2201, then the stimulator starts a respiratory timer 2202 and the time and amplitude values are stored. The respiratory timer will determine the amount of time in one given breathing cycle between the detected beginning of inspiration, exhalation and the detected beginning of the inspiration of the next cycle. The inspiration timer will also be started 2203. The inspiration timer will time the duration of inspiration when detected, as described with respect to step 2201, until the peak of the inspiration or the beginning of expiration.

The slope of the inspiration cycle is determined 2204 by determining the amplitude and time of that amplitude at a further point in time in the inspiration cycle (comp 2) from this information and the time and amplitude at the detection of the EMG (2201).

A peak detector monitors the integrated waveform and determines when it has peaked 2205, marking the end of inspiration and the beginning of expiration. When the peak is detected the time or duration of the inspiration cycle is stored along with the amplitude 2206. The inspiration timer is then turned off 2207 and the exhalation timer is started 2208. In step 2209 the values comp 3 and comp 4 are determined as a predetermined percentage to the peak value. In step 2210, a comparator will then compare the amplitude of the signal during exhalation to a predetermined value or percentage of the total amplitude as measured at the peak until that value is reached. This predetermined value is referred to herein as comp 3. The time is stored. In step 2211, a comparator will then compare the amplitude of the signal during exhalation to a predetermined lower end value or percentage of the total amplitude as measured at the peak until that value is reached. This predetermined value is referred to herein as comp 4. The stimulator then determines the slope of the exhalation cycle based on time and amplitude values of comp 3 and comp 4. The value for comp 4 may be selected to approximately mark the end of the fast exhalation period of the exhalation cycle, which is the initial period where the exhalation is sharper. At this point, the exhalation timer is stopped and the amplitude value and time is stored 2212. In step 2213, the stimulator may then determine the inhalation period, the exhalation period and the slope or curve characteristics of the breathing cycle during this time the slope of the waveform during either exhalation and/or inspiration may be recorded and analyzed to identify breathing irregularities. The inhalation period and exhalation period may be respectively based on the time values between the beginning of inhalation (comp 1) and the peak, and the peak (for inspiration) and the beginning of the peak and the end of the fast exhalation period. Also, the inspiration and expiration periods may also respectively include a calculation or approximation of the time between the actual beginning of inspiration to the detected beginning of inspiration and a calculation of the time between the end of the fast exhalation (comp 4) and the end of the exhalation period. The slopes of each of the inspiration periods and expiration periods may be calculated as well as the determination of other waveform characteristics that may provide useful diagnostic information. After the end of the fast exhalation period has been determined the stimulator then determines the total respirator period. After a first inhalation and exhalation cycle of a first breath, the stimulator awaits to detect a second cycle. The stimulator waits to detect the presence of a comp 1 value of an EMG 2215. If the EMG is present then the time is stored, the respiratory timer is stopped, and the respiratory period is stored 2216. The respiratory period may be a measured time from the detection of an EMG of a first waveform to the detection of an EMG of a second waveform. Alternatively, the respiratory period may be determined by adding the initial undetected period of the first waveform and subtracting the initial undetected period of the second waveform. The stimulator then determines if there is hyperventilation 2217 by determining if the rate is a certain value or amount above the intrinsic rate for the particular awake, sleep or other state of the patient. If hyperventilation is detected, then the stimulator goes to the hyperventilation module 2501 where hyperventilation is treated. If no hyperventilation is detected, the stimulator returns to its original monitoring step 2201 where it awaits the next EMG detection and repeats the cycle.

FIG. 24B illustrates the sleep apnea module 301. When sleep apnea is detected 2300, a determination is made as to whether apnea is complete apnea 2302. Complete apnea would be determined by a complete lack in effective or detected EMG (or alternatively, phrenic nerve activity). If the apnea is not sleep apnea then a determination is made as to whether the apnea is partial apnea 2320 where the EMG signal is attenuated a predetermined amount. If the apnea is obstructive apnea, an out of phase EMG may be detected as well.

If complete sleep apnea is detected 2302, then the pacing output parameters stored in RAM 2120 are loaded 2303, e.g., into a register. The pacing output is then delivered 2304. After delivering the pacing output to the phrenic nerve and/or diaphragm muscle, the EMG is observed 2305, if the EMG is not approximately at the intrinsic sleep level, then the parameters are adjusted to bring the EMG more within the appropriate range 2306 and elicit a response closer to intrinsic breathing. For example, if the frequency or amplitude is too low, then the frequency or amplitude of the pacing is adjusted upwards. If the frequency or amplitude is too high, then the frequency or amplitude of the pacing is adjusted downward. If the EMG is approximately at the intrinsic sleep level 2305, then the monitoring period is increased one second 2307 (e.g., the monitoring period may start at about 10 seconds with a maximum at about 15 seconds). The EMG is then monitored again to see if apnea is present 2308. If it is then the pacing output is continued 2304. If it is then, if the monitoring period is not at a defined maximum 2309 then the monitoring period is increased one second and the EMG is observed again 2308 and as long as the EMG is present 2308, the stimulator will keep increasing the monitoring period by one second 2307 until the maximum monitoring period is reached 2309. When the monitoring period does reach a maximum level, the apnea is confirmed as being treated 2310 by observing the EMG for a given period of time, e.g. for 3 consecutive EMG's. The parameters of stimulation and information regarding the episode are stored 2311 in event RAM 2119, and the system returns to EMG monitoring (step 2200 of FIG. 24A).

If complete sleep apnea is not detected 2302 then the stimulator determines if partial apnea is present 2320. If partial apnea is not present, the system returns to the emergency check 2250 to see if the system is malfunctioning. If partial apnea is present, then the existing EMG parameters are determined 2321 and the pacing parameters are adjusted based on the existing EMG 3222 and are loaded 2323 and are delivered 2324. The existing EMG parameters may be determined a number of ways. The system may attempt to match the desired EMG with the pacing output by adding on to the existing EMG. One method may involve calculating the tidal volume based on the peak value of the existing EMG voltage output, pulse width, thus area under the respiration curve; calculating the pacing energy (amplitude and frequency) required to achieve the tidal volume (of an intrinsic sleep EMG); and increasing the EMG or pacing an increased calculated amount to achieve the desired tidal volume.

If after delivering the pacing output 2324, the EMG is not at the intrinsic sleep level 2325, then the parameters are adjusted to elicit the intrinsic response 2331 and the parameters are loaded 3232 and delivered 2324 again. If the EMG is at the intrinsic sleep level 2325 then the monitoring period is increased by one second 2326, and EMG observed again to determine if the partial apnea has been treated 2327. If the apnea has not been treated, then the stimulator returns to delivering the pacing output 2324. If apnea has been treated and the monitoring period is not at the maximum 2328 then the monitoring time is increased by one second 2326, and partial apnea is detected 2327, etc. until the monitoring period has reached its maximum time 2328 throughout which apnea is determined to have been successfully treated. After the maximum period is reached apnea, treatment is confirmed 2329 by observing the EMG a predetermined period of time afterwards, e.g., for three consecutive EMG's. The parameters and information regarding the episode are then stored 2330. The system then returns to detecting the EMG (step 2200 of FIG. 24A)

Figure 24C:
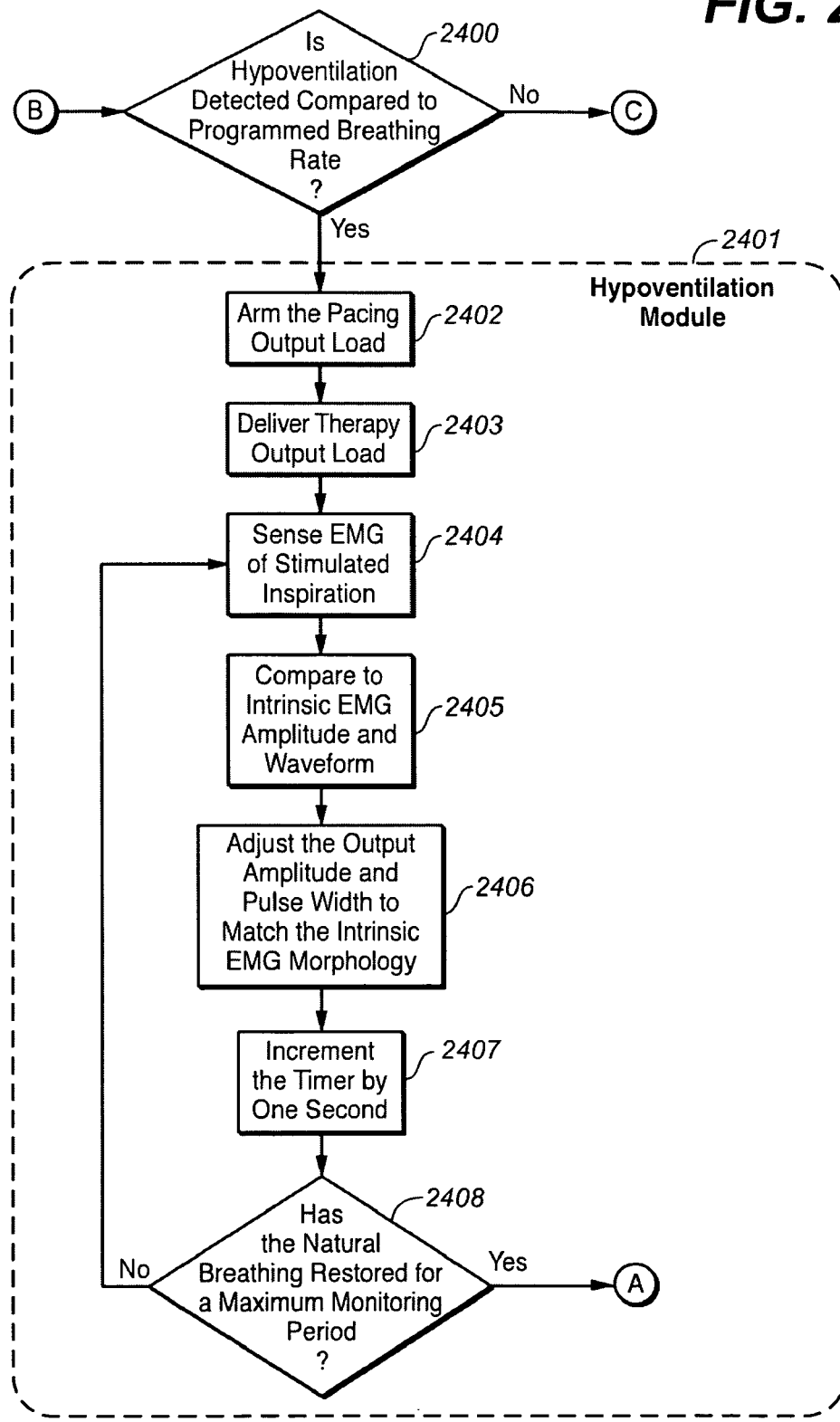

FIG. 24C illustrates the hypoventilation module 2401. After hypoventilation is detected 2400 by comparing the breathing rate to a programmed low threshold breathing rate for a particular condition or state (e.g., waking, resting or sleeping), a pacing output designed to elicit the intrinsic rate is loaded and is delivered to the phrenic nerve and/or diaphragm 2403. The EMG is then sensed 2404 and the EMG is compared to the intrinsic EMG amplitude and waveform 2405. The output of the amplitude, rate and pulse width are adjusted to match intrinsic EMG morphology 2406. The monitoring period is then increased by one second 2407. If the natural breathing rate has been restored for the maximum monitoring period, the stimulator returns to the step of detecting presence of EMG (step 2200, FIG. 24A). If it has not, then the EMG is sensed again 2404, compared to the intrinsic rate 2405, adjusted if necessary 2406, and the timer incremented again 2407 until the natural breathing has been restored. 2408.

Figure 24D:
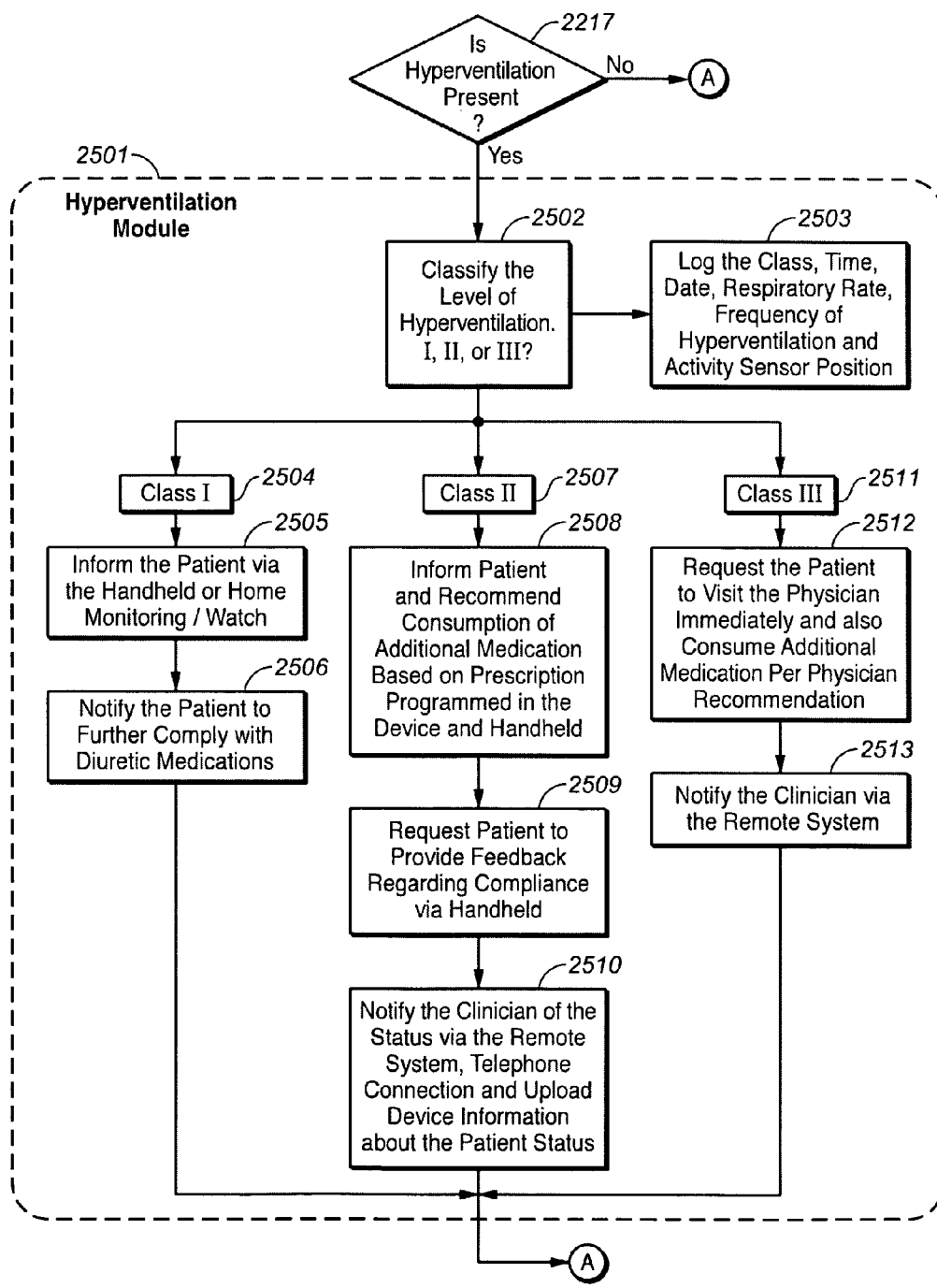

FIG. 24D illustrates the hyperventilation module 2501. If hyperventilation is present 2500, then the level of hyperventilation is classified as Class I (low), Class II (medium) or Class III (high) based on the rate an frequency of hyperventilation. These particular rates and classifications may vary from patient to patient and may be programmed in by the health care provider. The time date, respiratory rate, frequency of hyperventilation and activity sensor are sensed and stored in event RAM 2119. If class I is determined 2504, the patient is informed via the handheld or home monitoring device 2505 and the patient is notified to further comply with diuretic medications 2506. If class II is detected 2507, then the patient is informed and additional medication is recommended based on a prescription programmed into the hand held device 2508. The device then requests feedback by way of the hand held device, regarding compliance 2509. The health care provider is notified of the status by way of the remote system, telephone connection or otherwise, and the sensed information concerning the patient's status is uploaded 2510. If class III is detected 2511, then the patient is requested to visit the physician immediately and also to consume addition medication according to the physician's recommendation 2512. The health care provider is notified via the remote system 2512. The system then returns to detecting and EMG (step 2200, FIG. 24A).

Figure 16:
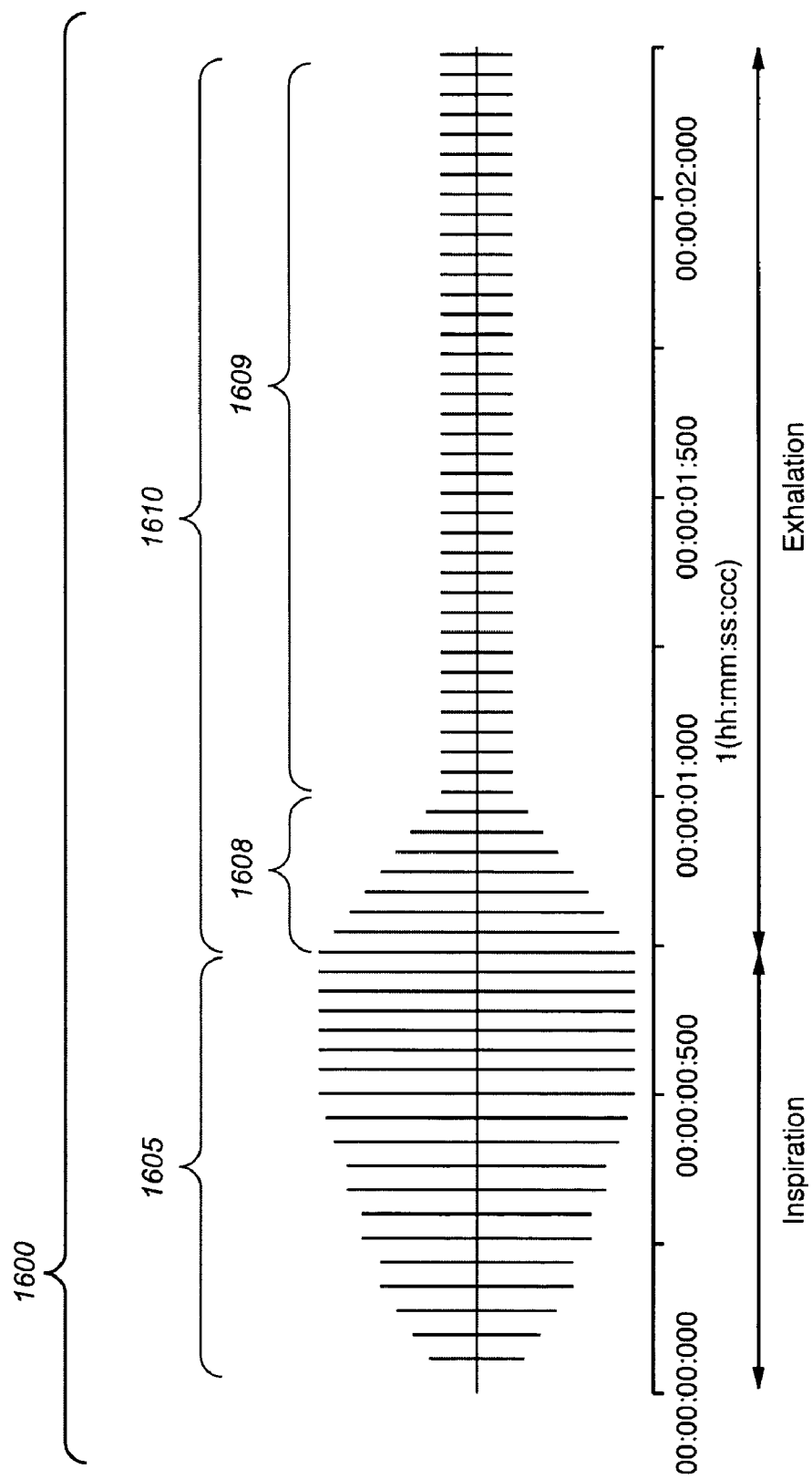
FIG. 16 shows a stimulation waveform for providing exhalation bias in accordance with the invention.

FIG. 16 shows a stimulation waveform diagram in accordance with the invention. A stimulation waveform 1600 comprises an inspiration stimulus 1605 and an exhalation bias waveform 1610. The inspiration stimulus 1605 is applied for the duration that a diaphragm stimulation has typically been applied. The exhalation bias waveform 1610 comprises a first tapering component 1608 followed by low level biased portion 1609. The exhalation bias waveform 1610 may be characterized by an frequency $f_b$ and an amplitude $A_b$.

In known diaphragm stimulation the diaphragm is allowed to relax completely during exhalation. This relaxation typically begins at the end of the inspiration stimulus and results in a minimum volume being established for the lungs and airways. By applying a low-level bias stimulus to the diaphragm during all or part of the rest period, an enhanced negative intrapleural pressure may be produced.

The enhanced negative pressure may used to increase the minimum volume for the lungs and airways. In certain circumstances it is believed that a greater minimum volume may relieve some of the gas exchange problems seen in disease states at lower resting lung volumes. The exhalation bias waveform 1610 provides a tool for modifying the lung volume during exhalation phase and rest period.

The exhalation bias waveform 1610 may be used to decrease the tidal volume, which may be used to decrease the minute ventilation and produce an increase in the partial pressure of $CO_2$.

In order to provide a smooth transition in the exhalation phase, the exhalation waveform component 1610 containing the first taper portion 1608 which comprises a negative ramp. The portion 1608 may be used to taper the exhalation. The low level bias stimulus portion 1609 provides a continuous low level enhanced negative intrapleural pressure. The portion 1609 may be applied all or a portion of an exhalation period.

The stimulation device may be used, for example in subjects with breathing disorders, heart failure patients and patients who cannot otherwise breathe on their own such as spinal cord injury patients.

Safety mechanisms may be incorporated into any stimulation device in accordance with the invention. The safety feature disables the device under certain conditions. Such safety features may include a patient or provider operated switch, e.g. a magnetic switch. In addition a safety mechanism may be included that determines when patient intervention is being provided. For example, the device will turn off if there is diaphragm movement sensed without an EMG as the case would be where a ventilator is being used.

While the invention has been described in detail with reference to preferred embodiments thereof, it will be apparent to one skilled in the art that various changes can be made, and equivalents employed, without departing from the scope of the invention.

What is claimed:

1. A system having an electrical stimulation device for treating a subject comprising:
   an electrode configured to be implanted and electrically coupled to tissue of a subject;
   a sensing device adapted to measure a respiration of the subject during a respiration cycle;
   a signal source coupled to the electrode configured to provide an electrical signal to tissue of the subject through the electrode wherein the electrical stimulation device is configured to electrically stimulate phrenic nerve or diaphragm tissue to cause a contraction of at least a portion of a diaphragm and,
   a control unit in communication with said signal source and sensing device,
   wherein the signal source is in communication with the sensing device and wherein the control unit is programmed to cause the signal source to generate a first stimulation signal correlated to a respiratory parameter of the subject and which is delivered by the signal source during spontaneous respiration by the subject at a level and a period effective to maintain contraction of the diaphragm to provide a therapeutically significant lung volume change and to modify negative intrapleural pressure around lungs of the subject during at least a portion of an exhalation period of the respiration cycle, said control unit is further programmed to compare sensed respiration parameters before and after delivery of said stimulation, and programmed to adjust a subsequent stimulation signal in amplitude and/or frequency if needed to cause a diaphragm movement.

2. The system of claim 1 wherein the control unit is programmed for the device to deliver the first or subsequent stimulation signal during a non-inspiratory portion of the subject's respiration cycle.

3. The system of claim 1 wherein said at least a portion of the exhalation period comprises the end of the subject's respiration cycle.

4. The system of claim 1 wherein the control unit is programmed for the device to deliver the first or subsequent stimulation signal configured to increase a minimum lung volume, wherein said signal source is adapted to provide an electrical signal comprising a burst or series of pulses.

5. The system of claim 1 wherein the signal source is configured to deliver a stimulation signal configured to cause a movement of a diaphragm having a normal respiratory function to thereby modify negative intrapleural pressure.

6. The system of claim 1 wherein the control unit is further programmed to cause the device to deliver a stimulation configured to provide a continuous low level enhanced negative intrapleural pressure.

7. The system of claim 1 wherein the control unit is further programmed to cause the device to deliver said stimulation signal for an entire exhalation cycle until the onset of a subsequent inspiration cycle.

8. The system of claim 7 wherein the control unit is programmed to cause the device to deliver the stimulation signal during inspiration and the entire exhalation cycle of the respiration cycle.

9. The system of claim 1 wherein the control unit is programmed to cause the device to deliver an electrical stimulation signal during an inspiratory portion of the subject's respiration cycle.

10. The system of claim 9 wherein the control unit is further programmed to deliver a first type of stimulation during and inspiration portion of a respiration cycle and a second type of stimulation during a non-inspiratory portion of the subject's respiration cycle.

11. The system of claim 1 wherein the signal is configured to cause a diaphragm movement to additionally provide a therapeutically significant lung volume change during at least a non-inspiratory portion of the subject's respiration cycle.

12. The system of claim 1 wherein the control unit is further programmed to generate the, first and/or subsequent stimulation signal which increases minute ventilation relative to a minute ventilation of un-stimulated respiration.

13. The system of claim 12 wherein the control unit is further programmed to cause the device to generate the first and/or subsequent stimulation signal which increases the minute ventilation by varying a combination of a respiratory rate and a tidal volume of the subject.

14. The system of claim 1 wherein the control unit is further programmed to cause the device to generate the first and/or subsequent stimulation signal which decreases minute ventilation relative to a minute ventilation of un-stimulated respiration.

15. The system of claim 14 wherein the control unit is further programmed to cause the device to generate the first and/or subsequent stimulation signal which decreases the minute ventilation by varying a combination of a respiratory rate and a tidal volume of the subject.

16. The system of claim 1 wherein the control unit is further programmed to cause the device to generate the first and/or subsequent stimulation signal which manipulates gas exchange wherein a level of $SaO_2$ or $PCO_2$ is increased.

17. A method of treating a subject comprising the steps of:
providing a device comprising a control unit, a stimulator having at least one implantable electrode capable of sensing respiratory parameters and delivering an electrical stimulation signal, and a signal source;
determining a respiratory parameter of a respiratory cycle of the subject utilizing said device;
modifying the respiratory parameter of the patient by electrically stimulating phrenic nerve or diaphragm tissue of the patient with a first stimulation signal comprising a burst or series of pulses delivered from the signal source via the electrode during spontaneous respiration by the subject to cause contraction of at least a portion of a diaphragm during at least a portion of exhalation at a level and a period effective to maintain contraction of the diaphragm and provide a modified negative intrapleural pressure and a therapeutically significant lung volume change; and
determining whether or not the therapeutically significant lung volume change has occurred to determine whether or not a second adjusted stimulation signal is needed.

18. The method of treating a patient of claim 17 wherein the step of modifying a respiratory parameter comprises modifying minute ventilation and further increasing a minimum lung volume of the subject.

19. The method of treating a patient of claim 17 wherein the step of modifying a respiratory parameter comprises stimulating to provide a continuous low level enhanced negative intrapleural pressure.

20. The method of treating a patient of claim 17 wherein the step of modifying a respiratory parameter comprises modifying intrapleural pressure for an entire exhalation cycle.

21. The method of treating a patient of claim 17 wherein the step of modifying a respiratory parameter comprises modifying minute ventilation for a duration including an inspiration cycle.

22. The method of treating a patient of claim 17 wherein the step of modifying a respiratory parameter comprises treating the patient having a disease state characterized at least in part by a gas exchange problem at a lower resting lung volume.

23. The method of treating a patient of claim 17 wherein the step of modifying a respiratory parameter comprises treating the patient with a breathing disorder.

24. The method of treating a patient of claim 23 wherein the step of treating the patient with a breathing disorder comprises treating the patient with sleep apnea.

25. The method of treating a patient of claim 23 wherein the step of treating the patient with a breathing disorder comprises treating the patient with obstructive sleep apnea.

26. The method of treating a patient of claim 23 wherein the step of treating the patient with a breathing disorder comprises treating the patient with hyperventilation.

27. The method of treating a patient of claim 23 wherein the step of treating the patient with a breathing disorder comprises treating the patient with hypoventilation.

28. The method of treating a patient of claim 23 wherein the step of treating the patient with a breathing disorder comprises treating the patient with partial apnea.

29. The method of treating a patient of claim 23 wherein the step of treating the patient with a breathing disorder comprises treating a heart failure patient.

30. The method of treating a patient of claim 17 wherein the step of modifying a respiratory parameter comprises providing stimulation to cause a diaphragm movement to provide a therapeutically significant lung volume change during at least a portion of a non-inspiratory period of the patient's respiration cycle.

31. The method of treating a patient of claim 17 wherein further electrically stimulating the diaphragm comprises applying the first and/or subsequent signal to vary a combination of a respiratory rate and a tidal volume such that a minute ventilation is increased relative to a minute ventilation of un-stimulated respiration.

32. The method of treating a patient of claim 17 wherein further electrically stimulating the diaphragm comprises applying the first and/or subsequent signal to vary a combination of a respiratory rate and a tidal volume such that a minute ventilation is decreased relative to a minute ventilation of un-stimulated respiration.

33. The method of claim 17 wherein modifying a respiratory parameter comprises manipulating gas exchange wherein a level of $SaO_2$ or $PCO_2$ is increased.

* * * * *